(12) United States Patent
Jain et al.

(10) Patent No.: US 11,796,541 B2
(45) Date of Patent: Oct. 24, 2023

(54) METHODS FOR ASSESSING MUCOSAL HEALING IN ULCERATIVE COLITIS DISEASE PATIENTS

(71) Applicant: Prometheus Laboratories Inc., San Diego, CA (US)

(72) Inventors: Anjali Jain, San Diego, CA (US); Venkateswarlu Kondragunta, San Diego, CA (US); Michael Hale, San Diego, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 86 days.

(21) Appl. No.: 17/483,462

(22) Filed: Sep. 23, 2021

(65) Prior Publication Data

US 2022/0082563 A1 Mar. 17, 2022

Related U.S. Application Data

(63) Continuation of application No. 16/614,752, filed as application No. PCT/IB2018/053923 on May 31, 2018, now Pat. No. 11,162,943.

(60) Provisional application No. 62/561,459, filed on Sep. 21, 2017, provisional application No. 62/512,947, filed on May 31, 2017.

(51) Int. Cl.
*G01N 33/564* (2006.01)
*G01N 33/68* (2006.01)

(52) U.S. Cl.
CPC ....... *G01N 33/564* (2013.01); *G01N 33/6893* (2013.01); *G01N 2800/065* (2013.01); *G01N 2800/52* (2013.01)

(58) Field of Classification Search
CPC ............. G01N 33/564; G01N 33/6893; G01N 2800/065; G01N 2800/52
See application file for complete search history.

(56) References Cited

U.S. PATENT DOCUMENTS

| | | | |
|---|---|---|---|
| 5,674,754 A | 10/1997 | Ahrens et al. | |
| 6,319,899 B1 | 11/2001 | Schwartz | |
| 7,252,971 B2 | 8/2007 | Benson et al. | |
| 7,932,372 B2 | 4/2011 | Pullen et al. | |
| 8,012,698 B2 | 9/2011 | Stephens et al. | |
| 8,165,819 B2 | 4/2012 | Clermont et al. | |
| 8,293,489 B2 | 10/2012 | Henkin | |
| 8,538,774 B2 | 9/2013 | Michelson et al. | |
| 8,630,810 B2 | 1/2014 | Clermont et al. | |
| 9,732,385 B2 | 8/2017 | Barken et al. | |
| 10,086,072 B2 | 10/2018 | Singh et al. | |
| 11,162,943 B2 | 11/2021 | Jain et al. | |
| 2002/0025553 A1 | 2/2002 | Wei | |
| 2003/0087285 A1 | 5/2003 | Chow et al. | |
| 2004/0197304 A1 | 10/2004 | Chen et al. | |
| 2005/0154536 A1 | 7/2005 | Chow et al. | |
| 2006/0216239 A1 | 9/2006 | Zhang et al. | |
| 2008/0086272 A1 | 4/2008 | Fillet | |
| 2008/0162101 A1 | 7/2008 | Sarna et al. | |
| 2008/0228456 A1 | 9/2008 | Clermont et al. | |
| 2009/0156418 A1 | 6/2009 | Blank et al. | |
| 2010/0255513 A1* | 10/2010 | Denson | G01N 33/6863 435/7.1 |
| 2011/0045476 A1 | 2/2011 | Barken et al. | |
| 2011/0059445 A1 | 3/2011 | Rutgeerts et al. | |
| 2012/0046197 A1 | 2/2012 | Glezer et al. | |
| 2013/0071860 A1 | 3/2013 | Hale et al. | |
| 2013/0224210 A1 | 8/2013 | Adamkewicz et al. | |
| 2013/0273566 A1 | 10/2013 | Denson et al. | |
| 2014/0113306 A1 | 4/2014 | Haimovich et al. | |
| 2014/0141983 A1 | 5/2014 | Singh et al. | |
| 2014/0236166 A1 | 8/2014 | Park et al. | |
| 2014/0329721 A1 | 11/2014 | Joern et al. | |
| 2014/0356882 A1 | 12/2014 | Moses et al. | |
| 2015/0072879 A1 | 3/2015 | Princen et al. | |
| 2015/0301055 A1 | 10/2015 | Spetzler | |
| 2015/0355195 A1 | 12/2015 | Singh et al. | |
| 2017/0360926 A1 | 12/2017 | Rosario et al. | |
| 2017/0368027 A1 | 12/2017 | Blum-Sperisen et al. | |

(Continued)

FOREIGN PATENT DOCUMENTS

| CA | 2772916 A1 | 3/2011 |
|---|---|---|
| CN | 1764838 A | 4/2006 |

(Continued)

OTHER PUBLICATIONS

Algaba et al.: Relationship between levels of angiogenic and lymphangiogenic factors and the endoscopic, histological and clinical activity, and acute-hase reactants in patients with inflammatory bowel disease. J Crohns Colitis. 7(11:e569-79 (2013).

Baugh et al.: Matrix metalloproteinase levels are elevated in inflammatory bowel disease. Gastroenterology. 117:814-822 (1999).

Breiman et al.: Chapter 6 Medical diagnosis and prognosis. Classification and regression trees. Chappman & Hall/CRC (1984) (pp. 174-346).

Breiman: Random Forests. Machine Learning, 45; 5-32 (2001) http://stat-www.berkeley.edu/users/breiman/RandomForests/cc_home.htm.

Carman et al.: Clinical disease activity and endoscopic severity correlate poorly in children newly diagnosed with Crohn's disease. Gastrointest Endosc. 89(2):364-372 (2019).

(Continued)

*Primary Examiner* — Changhwa J Cheu
(74) *Attorney, Agent, or Firm* — Wilson Sonsini Goodrich & Rosati

(57) ABSTRACT

The present disclosure provides methods for assessing mucosal healing in a patient with Crohn's Disease. The methods include detecting expression levels of analytes in a serum sample from a patient, and applying a mathematical algorithm to the expression levels, thereby producing a Mucosal Healing Index score for the patient. The present disclosure also provides kits that include two or more binding partners, each or which is capable of binding a different analyte measured in the disclosed mucosal healing assessment methods.

20 Claims, 10 Drawing Sheets

(56) References Cited

U.S. PATENT DOCUMENTS

| | | | |
|---|---|---|---|
| 2018/0086833 | A1 | 3/2018 | Hassanali et al. |
| 2019/0060449 | A1 | 2/2019 | Singh et al. |
| 2022/0096629 | A1 | 3/2022 | Singh et al. |

FOREIGN PATENT DOCUMENTS

| | | | | |
|---|---|---|---|---|
| CN | 1839157 | A | 9/2006 | |
| CN | 101291693 | A | 10/2008 | |
| CN | 101472611 | A | 7/2009 | |
| EP | 1725876 | B1 | 5/2009 | |
| JP | 2006521537 | A | 9/2006 | |
| RU | 2141332 | C1 | 11/1999 | |
| WO | WO-2004037073 | A2 * | 5/2004 | ....... G01N 33/56972 |
| WO | WO-2004090539 | A2 | 10/2004 | |
| WO | WO-2005000897 | A2 | 1/2005 | |
| WO | WO-2005009339 | A2 * | 2/2005 | ......... G01N 33/6893 |
| WO | WO-2007050607 | A2 | 5/2007 | |
| WO | WO-2007149814 | A1 | 12/2007 | |
| WO | WO-2008036802 | A2 | 3/2008 | |
| WO | WO-2009012140 | A2 | 1/2009 | |
| WO | WO-2009108637 | A1 | 9/2009 | |
| WO | WO-2010025340 | A2 | 3/2010 | |
| WO | WO-2010132723 | A1 | 11/2010 | |
| WO | WO-2010151699 | A1 | 12/2010 | |
| WO | WO-2011008990 | A1 | 1/2011 | |
| WO | WO-2011047358 | A1 | 4/2011 | |
| WO | WO-2011050069 | A1 | 4/2011 | |
| WO | WO-2011066458 | A2 | 6/2011 | |
| WO | WO-2011153501 | A2 | 12/2011 | |
| WO | WO-2012088337 | A1 | 6/2012 | |
| WO | WO-2012119113 | A2 | 9/2012 | |
| WO | WO-2012154987 | A1 | 11/2012 | |
| WO | WO-2013033623 | A1 | 3/2013 | |
| WO | WO-2013059732 | A1 * | 4/2013 | ........... C12Q 1/6883 |
| WO | WO-2014054013 | A1 | 4/2014 | |
| WO | WO-2015110989 | A1 | 7/2015 | |
| WO | WO-2018220588 | A1 | 12/2018 | |
| WO | WO-2020117795 | A1 | 6/2020 | |

OTHER PUBLICATIONS

Chambers et al.: Serum amyloid A protein compared with C-reactive protein, alpha 1-antichymotrypsin and alpha 1-acid glycoprotein as a monitor of inflammatory bowel disease. European Journal of Clinical Investigation. 17(5):460-467 (1987).
Christensen et al.: Understanding endoscopic disease activity in IBD: how to incorporate it into practice. Curr Gastroenterol Rep. 18(1):5 (2016).
Cristianini et al.: An introduction to Support Vector Machines and Other Kernel-Based Learning Methods. Cambridge University Press; (2000) https://www.google.com/books/edition/An_Introduction_to_Support_Vector_Machin/_PXJn_cxv0AC?hl=en&gbp.
Daperno et al.: Results of the 2nd part scientific workshop of the ECCO (II): Measures and markers of prediction to achieve, detect, and monitor intestinal healing in inflammatory bowel disease. Journal of Crohn's and Colitis. 5:484-498 (2011).
Daperno et al.: Development and validation of a new, simplified endoscopic activity score for Crohn's disease: the SES-CD. Gastrointestinal Endoscopy. 60(4):505-512 (2004).
Dave et al.: Mucosal healing in inflammatory bowel disease—A true paradigm of success?. Gastroenterology & Hepatology. 8(1):29-38 (2012).
De Bruyn et al.: Biomarker Panel for Prediction of Mucosal Healing in Patients With Crohn's Disease Under Infliximab Therapy. Biosciences Information Service (2014).
D'Haens et al.: Development and Validation of a Test to Monitor Endoscopic Activity in Patients with Crohn's Disease Based on Serum Levels of Proteins. Gastroenterology. vol. Pii:S0016-5085(19)41525-4 (2019).
DiSabatino et al.: Stromelysin-1 and macrophage metalloelastase expression in the intestinal mucosa of Crohn's disease patients treated with infliximab. European Journal of Gastroenterology and Hepatology. 21(9):1049-55 (2009).
Efsen et al.: Ramiprilate Inhibits Functional Matrix Metalloproteinase Activity in Crohn's Disease Fistulas. Basic and Clinical Pharmacy and Toxicology. 109(3):208-216 (2011).
Epstein et al.: Curcumin suppresses p38 mitogen-activated protein kinase activation, reduces IL-1b and matrix metalloproteinase-3 and enhances IL-10 in the mucosa of children and adults with inflammatory bowel disease. British Journal of Nutrition. 103:824-832 (2010).
European Patent Application No. 19212960.9 Extended European Search Report dated Mar. 24, 2020.
Ferrante et al.: Validation of Endoscopic Activity Scores in Patients with Crohn's Disease Based on a Post Hoc Analysis of Data From SONIC. Gastroenterology. 145(5):978-986 (2013).
Freeman et al.: Neural Networks: Algorithms, Applications and Programming Techniques. Addison-Wesley Publishing Company; 414 pages (1991).
Froslie et al.: Mucosal healing in inflammatory bowel disease: Results from a Norwegian populaiton-based cohort. Gastroenterology. 133:412-422 (2007).
Geboes et al.: Endoscopic and histologic evidence of persistent mucosal healing and correlation with clinical improvement following sustained infliximab treatment for Crohn's disease. Current Medical Research and Opinion. 21(11):1741-54 (2005).
Ghosh et al.: Anti-TNF therapy in Crohn's disease Novartis Foundation Symposium 263:193-218 (2004).
Gordon et al.: CC-10004 but not thalidomide or lenalidomide inhibits lamina propria mononuclear cell TNF-$\alpha$ and MMP-3 production in patients with inflammatory bowel disease. Journal of Crohn's and Colitis. 175-182 (2009).
Hassoun. Fundamentals of Artificial Neural Networks. MIT Press, Cambridge, Massachusetts, London (1995) https://www.google.com/books/edition/Fundamentals_of_Artificial_Neural_Networ/Otk32Y3QkxQC?hl=en&gbp.
Hu et al.: Research Progress of Inflammatory Bowel Disease. Basic and Clinical Medicine, Guangdong Science & Technology Press, Ltd.; pp. 46-47 (2006) machine translation.
International Application No. PCT/IB2013/059077 International Preliminary Report on Patentability dated Apr. 7, 2015.
International Application No. PCT/IB2013/059077 International Search Report and Written Opinion dated Dec. 5, 2013.
International Application No. PCT/IB2018/053923 International Search Report and Written Opinion dated Jul. 27, 2018.
International Application No. PCT/US2012/037375 International Search Report and Written Opinion dated Aug. 16, 2012.
Jiang et al.: Study on anti-tumor necrosis factor antibody for the treatment of inflammatory bowel disease. Clinical Medication Journal. 9(2):16-20 (2011).
Kelly et al.: Development and validation of a multi-marker serum test for the assessment of mucosal healing in Crohn's disease patients. American College of Gastroenterology. (2017).
Lewis: The utility of biomarkers in the diagnosis and therapy of inflammatory bowel disease. Gastroenterology. 140:1817-1826 (2011).
Li et al.: The effect of hepatocyte growth factor (Hgf) on mucosal morphology and absorption after rat small intestine transplantation. Medical Journal of Chinese People's Liberation Army. 25(4):242-244 (2000).
Moskovitz et al.: Defining and validating cut-offs for the Simple Endoscopic Score for Crohn's Disease. Gastroenterology. 132:S1097 (2007).
Neurath et al.: Mucosal healing in inflammatory bowel diseases: a systematic review. Gut. 61:1619-1635 (2012).
Noble et al.: Regional variation in gene expression in the healthy colon is dysregulated in ulcerative colitis. Gut. 57:1398-1405 (2008).
Oliva et al.: Endoscopy in Pediatric Inflammatory Bowel Disease: A Position Paper on Behalf of the Porto IBD Group of the European Society for Pediatric Gastroenterology, Hepatology and Nutrition. J Pediatr Gastroenterol Nutr. 63(3):414-430 (2018).
Ouyang: Editor-in-chief, Research Advances in Inflammatory Bowel Disease. Chengdu: Sichuan Science and Technology Press. pp. 207-210 (2000).

(56) References Cited

OTHER PUBLICATIONS

PCT/US2019/064224 International Search Report and Written Opinion dated Feb. 12, 2020.
Peyrin-Biroulet et al.: Selecting therapeutic targets in inflammatory bowel disease (STRIDE): determining therapeutic goals for treat-to-target. Am J Gastroenterol. 110(9):1324-1338 (2015).
Prometheus® Monitr™ Crohn's Disease Cat. #7300. Prometheus® Therapeutics & Diagnostics website (2018).
Scaldaferri et al.: Mucosal biomarkers in inflammatory bowel disease: Key pathogenic players or disease predictors?. World Journal of Gastroenterology. 16(21):2616-2625 (2010).
Schoepfer et al.: Monitoring inflammatory bowel disease activity: clinical activity is judged to be more relevant than endoscopic severity or biomarkers. Journal of Crohn's and Colitis. 6:412-418 (2012).
Sipponen et al.: Endoscopic evaluation of Crohn's disease activity: Comparison of the CDEIS and the SES-CD. Inflamm Bowel Dis. 16:2131-2136 (2010).
Steinberg et al.: CART: Tree Structured Non-Parametric Data Analysis. Salford Systems. 355 pages (1995).
Toedter et al.: Relationship of C-Reactive Protein With Clinical Response After Therapy With Ustekinumab in Crohn's Disease. American Journal of Gastroenterology. 104(11):2768-2773 (2009).
Tutina et al.: Lechebnoe pitanie pri nespetsificheskom yazvennom kolite i bolezni Krona u detei [Nutritional therapy for nonspecific ulcerative colitis and Crohn's disease in children]. Pediatricheskaya farmakologiya. 5(5):110-115 (2008).
U.S. Appl. No. 16/112,242 Final Office Action dated Apr. 14, 2021.
U.S. Appl. No. 16/112,242 Office Action dated Sep. 3, 2020.
U.S. Appl. No. 16/614,752 Final Office Action dated Sep. 22, 2020.
U.S. Appl. No. 16/614,752 Office Action dated Apr. 9, 2021.
U.S. Appl. No. 16/614,752 Office Action dated Jun. 11, 2020.
Vuitton et al.: IOIBD technical review on endoscopic indices for Crohn's disease clinical trials. Gut. 65(9):1447-1455 (2016).
Zadeh: Fuzzy Sets. Information and Control; 8:338-353 (1965).

* cited by examiner

*14% of samples fall into MHI 41-49

| MHI Diagnostic Performance | |
|---|---|
| Accuracy | 90% (95%CI: 87% to 93%) |
| Sensitivity | 82% (95%CI: 75% to 89%) |
| Specificity | 94% (95%CI: 91% to 97%) |
| PPV | 87% (95%CI: 80% to 93%) |
| NPV | 92% (95%CI: 88% to 95%) |

FIG. 2C

| | ALL PATIENTS (TAILORIX) (N = 412) | ILEAL ONLY (n = 96) | ILEOCOLONIC (N = 244) | COLONIC ONLY (N = 72) |
|---|---|---|---|---|
| Patients [n (%)] | 118 (100%) | 27 (22.9%) | 71 (60.2%) | 20 (16.9%) |
| Accuracy | 90% (95% CI: 87% to 93%) | 95% (95% CI: 88% to 99%) | 90% (95% CI: 85% to 94%) | 87% (95% CI: 77% to 94%) |
| Sensitivity | 82% (95% CI: 75% to 89%) | 86% (95% CI: 65% to 97%) | 80% (95% CI: 69% to 89%) | 89% (95% CI: 67% to 99%) |
| Specificity | 94% (95% CI: 91% to 97%) | 98% (95% CI: 91% to 100%) | 95% (95% CI: 90% to 98%) | 86% (95% CI: 73% to 95%) |
| PPV | 87% (95% CI: 80% to 93%) | 95% (95% CI: 73% to 99%) | 89% (95% CI: 80% to 94%) | 74% (95% CI: 57% to 86%) |
| NPV | 92% (95% CI: 88% to 95%) | 95% (95% CI: 87% to 98%) | 90% (95% CI: 85% to 94%) | 95% (95% CI: 84% to 99%) |

FIG. 2D

| MHI DIAGNOSTIC PERFORMANCE | |
|---|---|
| Accuracy*[1] | 90% <br> *(95% CI: 85% to 94%)* |
| Sensitivity | 89% <br> *(95% CI: 81% to 94%)* |
| Specificity | 91% <br> *(95% CI: 84% to 96%)* |
| PPV | 90% <br> *(95% CI: 84% to 94%)* |
| NPV | 89% <br> *(95% CI: 83% to 93%)* |

*Accuracy (% correct calls) = [(TP + TN)/Total Samples]
[1] Accuracy for Validation of MH Cohort 1 was also 90% (95% CI: 87% to 93%)
See, Example 6.

METHODS FOR ASSESSING MUCOSAL
HEALING IN ULCERATIVE COLITIS
DISEASE PATIENTS

CROSS-REFERENCES TO RELATED APPLICATIONS

This application is a continuation of U.S. application Ser. No. 16/614,752, filed Nov. 18, 2019, which is now issued as U.S. Pat. No. 11,162,943 on Nov. 2, 2021, which is a 371 U.S. National Phase of International Application No. PCT/M2018/053923, filed May 31, 2018, which claims priority to U.S. Provisional Application No. 62/512,947 filed May 31, 2017, and U.S. Provisional Application No. 62/561,459, filed Sep. 21, 2017, the disclosures of which are incorporated herein by references in their entirety for all purposes.

BACKGROUND

Crohn's disease (CD) recurs in a majority of patients after intestinal resection, with new lesions developing at the anastomosis in 70-90% of patients within 1 year of surgery. Mucosal healing (MH), typically defined as absence of ulcers on visual endoscopic examination, is a desired clinical endpoint that has become the primary therapeutic target in CD. Ileocolonoscopy, currently the gold standard for assessing MH, is however an invasive and time consuming procedure with poor patient acceptance. This limits the practical feasibility for serial monitoring of mucosal disease activity and the MH status in response to treatment. Non-invasive monitoring of post-operative disease recurrence would be useful in the clinical management of such patients but is particularly challenging due to low disease burden after removal of macroscopically involved intestine. In particular, non-invasive alternative tests could provide an attractive option as adjuncts or surrogates for endoscopy for inflammatory bowel disease (IBD) patient management, with particular utility in patients with CD given its transmural nature and lack of optimal endoscopic accessibility of the small bowel. The present disclosure addresses this and other needs and provides related advantages.

BRIEF SUMMARY

In one aspect, the present disclosure provides a method for assessing mucosal healing in a patient with Crohn's Disease (CD). The method includes providing a serum sample from a patient. The method further includes detecting in the serum sample an expression level of each of two or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. The method further includes applying a mathematical algorithm to the expression levels of the two or more biomarkers, thereby producing a Mucosal Healing Index (MHI) score for the patient. In certain aspects, the MHI score has a scale from 0 to 100.

In some embodiments, the detecting includes contacting the serum sample with a binding partner for each of the two or more biomarkers and detecting binding between each biomarker and its respective binding partner. In certain aspects, each binding partner is an antibody. In some embodiments, the detecting includes measuring an expression level of each of the biomarkers in the group consisting of Ang1, Ang2, CEACAM1, VCAM1, TGFα, CRP, SAA1, MMP-1, MMP-2, MMP-3, MMP-9, EMMPRIN, and IL-7. In certain aspects, the method further includes determining that the patient has a high probability of being in remission or having mild endoscopic disease when the MHI score is less than or equal to 40. In certain embodiments, the high probability of being in remission or having mild endoscopic disease is greater than or equal to 92%. In some aspects, the remission corresponds to a Crohn's Disease Endoscopic Index of Severity (CDEIS) of less than 3 (CDEIS <3). In some embodiments, the mild endoscopic disease corresponds to a CDEIS of between 3-8 (CDEIS 3-8). In certain aspects, the method further includes determining that the patient has a high probability of having endoscopically active disease when the MHI score is greater than or equal to 50. In certain embodiments, the high probability of having endoscopically active disease is greater than or equal to 87%. In some aspects, the endoscopically active disease corresponds to a CDEIS of greater than or equal to 3 (CDEIS ≥3). In some aspects, the method further includes determining that the patient has a moderate probability of having endoscopically active disease when the MHI score is between 40 and 50. In some embodiments, the moderate probability of having endoscopically active disease is greater than or equal to 78%.

In certain aspects, the mathematical algorithm includes two or more models relating the expression levels of the biomarkers to an endoscopic score. In certain embodiments, one or more of the two or more models are derived by using classification and regression trees, and/or one or more of the two or more models are derived by using ordinary least squares regression. In certain embodiments, one or more of the two or more models are derived by using classification and regression trees, and/or one or more of the two or more models are derived by using ordinary least squares regression to model diagnostic sensitivity. In certain embodiments, one or more of the two or more models are derived by using classification and regression trees, and/or one or more of the two or more models are derived by using ordinary least squares regression to model diagnostic specificity. In certain embodiments, one or more of the two or more models are derived by using classification and regression trees, and/or one or more of the two or more models are derived by using ordinary least squares regression to model diagnostic specificity. In certain embodiments, one or more of the two or more models are derived by using classification and regression trees to model diagnostic specificity, and/or one or more of the two or more models are derived by using ordinary least squares regression. In certain embodiments, one or more of the two or more models are derived by using classification and regression trees to model diagnostic sensitivity, and/or one or more of the two or more models are derived by using ordinary least squares regression. In certain embodiments, one or more of the two or more models are derived by using classification and regression trees to model diagnostic specificity, and/or one or more of the two or more models are derived by using ordinary least squares regression to model diagnostic sensitivity.

In certain embodiments, one or more of the two or more models are derived by using random forest learning classification, and/or one or more of the two or more models are derived by using quantile classification. In certain embodiments, one or more of the two or more models are derived by using random forest learning classification to model diagnostic sensitivity, and/or one or more of the two or more models are derived by using quantile classification. In certain embodiments, one or more of the two or more models are derived by using random forest learning classification to model diagnostic specificity, and/or one or more of the two or more models are derived by using quantile classification.

In certain embodiments, one or more of the two or more models are derived by using random forest learning classification, and/or one or more of the two or more models are derived by using quantile classification to model diagnostic sensitivity. In certain embodiments, one or more of the two or more models are derived by using random forest learning classification, and/or one or more of the two or more models are derived by using quantile classification to model diagnostic specificity. In certain embodiments, one or more of the two or more models are derived by using random forest learning classification to model diagnostic specificity, and/or one or more of the two or more models are derived by using quantile classification to model diagnostic sensitivity. In certain embodiments, one or more of the two or more models are derived by using random forest learning classification to model diagnostic specificity, and/or one or more of the two or more models are derived by using quantile classification to model diagnostic sensitivity. In certain embodiments, one or more of the two or more models are derived by using logistic regression to model diagnostic sensitivity, and one or more of the two or more models are derived by using logistic regression to model diagnostic specificity.

In some aspects, the patient is receiving biologic or non-biologic therapy. In some embodiments, the method assesses mucosal healing by determining the efficacy of the therapy. In certain aspects, the method assesses mucosal healing at colonic, ileocolonic, and/or ileal disease locations in the patient. In certain embodiments, the method assesses mucosal healing in the patient after surgery. In some embodiments, the method assesses mucosal healing by identifying post-operative, endoscopic recurrence in the patient. In certain aspects, the method assesses mucosal healing by predicting or monitoring the mucosal status in the patient.

In another aspect, the disclosure provides a method for assessing mucosal healing in a patient with CD. The method includes: (a) detecting the expression of the following biomarkers in a serum sample from the patient: Ang1; Ang2; CEACAM1; VCAM1; TGFα; CRP; SAA1; MMP-1; MMP-2; MMP-3; MMP-9; EMMPRIN; and IL-7. The method further includes: (b) applying a mathematical algorithm to the expression of the biomarkers in step (a) to produce an MHI for the patient, wherein the MHI is a scale of 0-100, wherein the patient is in remission or has mild endoscopic disease when the MHI is between 0-40, and wherein the patient has endoscopically active disease when the MHI is between 50-100.

In some embodiments, the patient is receiving biologic or non-biologic therapy. In certain aspects, the method assesses mucosal healing by determining the efficacy of the therapy. In certain embodiments, the method assesses mucosal healing at colonic, ileocolonic, and/or ileal disease locations in the patient. In some aspects, the method assesses mucosal healing by identifying post-operative, endoscopic recurrence in the patient. In some embodiments, the remission corresponds to a CDEIS of less than 3 (CDEIS <3). In certain aspects, the mild endoscopic disease corresponds to a CDEIS of between 3-8 (CDEIS 3-8). In some embodiments, the endoscopically active disease corresponds to a CDEIS of greater than or equal to 3 (CDEIS ≥3). In certain aspects, the method assesses mucosal healing by predicting or monitoring the mucosal status in the patient.

In another aspect, the disclosure is to a method of evaluating the efficacy of a therapy administered to a patient with CD. The method includes providing a serum sample from the patient. The method further includes detecting in the serum sample an expression level of each of two or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. The method further includes applying a mathematical algorithm to the expression levels of the two or more biomarkers, thereby producing an MHI score for the patient. The method further includes adjusting the therapy in response to the MHI score.

In some embodiments, the detecting includes contacting the serum sample with a binding partner for each of the two or more biomarkers and detecting binding between each biomarker and its respective binding partner. In certain aspects, each binding partner is an antibody. In some embodiments, the adjusting includes decreasing the therapy when the MHI score is less than or equal to 40 on a scale from 0 to 100. In certain aspects, the adjusting includes increasing the therapy when the MHI score is greater than or equal to 50 on a scale from 0 to 100. In certain embodiments, the therapy comprises one or more biologic agents, conventional drugs, nutritional supplements, or combinations thereof.

In another aspect, the disclosure is to a method of detecting in a patient with Crohn's disease an expression level of two or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. The method includes obtaining a serum sample from the patient. The method further includes detecting the expression level of each of the two or more biomarkers in the serum sample by contacting the serum sample with a binding partner for each of the two or more biomarkers and detecting binding between each biomarker and its respective binding partner. In some embodiments, each binding partner is an antibody.

In another aspect, the disclosure is to a method for assessing mucosal healing in a patient with Crohn's disease. The method includes obtaining a serum sample from the patient. The method further includes detecting the expression level of each of the two or more biomarkers in the serum sample by contacting the serum sample with a binding partner for each of the two or more biomarkers and detecting binding between each biomarker and its respective binding partner. Each of the two or more biomarkers can independently be Ang1, Ang2, CEACAM1, VCAM1, TGFα, CRP, SAA1, MMP-1, MMP-2, MMP-3, MMP-9, EMMPRIN, or IL-7. The method further includes applying a mathematical algorithm to the expression levels of the two or more biomarkers, thereby producing an MHI score for the patient.

In some embodiments, each binding partner is an antibody. In certain aspects, the method further includes determining that the patient has a high probability of being in remission or having mild endoscopic disease when the MHI score is less than or equal to 40 on a scale from 0 to 100. In certain embodiments, the method further includes determining that the patient has a high probability of having endoscopically active disease when the MHI score is greater than or equal to 50 on a scale from 0 to 100.

In another aspect, the disclosure is to a method for assessing mucosal heling in a patient with Crohn's disease and treating Crohn's disease in the patient. The method includes obtaining a serum sample from a patient. The method further includes detecting in the serum sample an expression level of each of two or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. The method further includes applying a mathematical algorithm to the expression levels of the two or more biomarkers, thereby producing an MHI score for the patient. The method further includes diagnosing the patient with a high probability of having endoscopically active disease when the MHI score is greater than or equal to 50 on a scale from 0 to 100. The method further includes administering an effective amount of a therapeutic agent to the diagnosed patient. In some embodiments, the therapeutic agent includes one or more biologic agents, conventional drugs, nutritional supplements, or combinations thereof.

In another aspect, the disclosure is to a method of treating a patient with Crohn's Disease. The method includes administering an effective amount of a therapeutic agent to a patient diagnosed with a high probability of having endoscopically active disease according to a disclosed method. In some embodiments, the therapeutic agent comprises one or more biologic agents, conventional drugs, nutritional supplements, or combinations thereof.

In another aspect, the disclosure provides a kit including two or more binding partners Each of the two or more binding partners is attached to one or more solid supports. Each of the two or more binding partners is also capable of binding a different analyte selected from the group consisting of Ang1, Ang2, CEACAM1, VCAM1, TGFα, CRP, SAA1, MMP-1, MMP-2, MMP-3, MMP-9, EMMPRIN, and IL-7.

In some embodiments, each of the two or more binding partners is covalently attached to one or more solid supports. In certain aspects, each of the two or more binding partners is attached to a different solid support. In some embodiments, the kit further includes instructions for contacting the one or more solid supports with a serum sample from a patient. The instructions can further be for detecting in the serum sample an expression level of each of analytes bound by the one or more binding partners. The instructions can further be for applying a mathematical algorithm to the expression levels of the analytes, thereby producing an MHI score for the patient. In certain aspects, the MHI score has a scale from 0 to 100.

In some embodiments, the instructions can further be for determining that the patient has a high probability of being in remission or having mild endoscopic disease when the MHI score is less than or equal to 40. In certain aspects, the high probability of being in remission or having mild endoscopic disease is greater than or equal to 92%. In certain embodiments, the remission corresponds to a CDEIS of less than 3 (CDEIS <3). In some aspects, the mild endoscopic disease corresponds to a CDEIS of between 3-8 (CDEIS 3-8). In certain aspects, the instructions can further be for determining that the patient has a high probability of having endoscopically active disease when the MHI score is greater than or equal to 50. In some embodiments, the high probability of having endoscopically active disease is greater than or equal to 87%. In certain aspects, the endoscopically active disease corresponds to a CDEIS of greater than or equal to 3 (CDEIS ≥3). In certain embodiments, the instructions can further be for determining that the patient has a moderate probability of having endoscopically active disease when the MHI score is between 40 and 50. In some aspects, the moderate probability of having endoscopically active disease is greater than or equal to 78%.

In some embodiments, the patient is receiving biologic or non-biologic therapy. In certain aspects, the kit assesses mucosal healing by determining the efficacy of the therapy. In certain embodiments, the kit assesses mucosal healing at colonic, ileocolonic, and/or ileal disease locations in the patient. In some aspects, the kit assesses mucosal healing in the patient after surgery. In some embodiments, the kit assesses mucosal healing by identifying post-operative, endoscopic recurrence in the patient. In certain aspects, the kit assesses mucosal healing by predicting or monitoring the mucosal status in the patient.

Other objects, features, and advantages of the present disclosure will be apparent to one of skill in the art from the following detailed description and figures.

BRIEF DESCRIPTION OF THE DRAWINGS

FIGS. 2A-2D show the development and validation of the MHI. 90% concordance with endoscopic assessment of mucosal disease activity was observed. FIG. 2A: Serum samples from 396 CD patients were divided into training (cohorts 1-4) and validation (cohort 5) sets. Multiple logistic regression equations were used to develop a 13-biomarker model against endoscopic disease activity, termed as MHI, that was validated on an independent, longitudinal cohort. FIG. 2B: Description of MHI 0-40 and MHI 50-100 score ranges. MHI diagnostic performance in the overall validation cohort (FIG. 2C) and according to disease location (FIG. 2D) are shown.

FIG. 3A: Case Study #1; FIG. 3B: Case Study #2; FIG. 3C: Case Study #3.

FIG. 8A: Agreement between CDEIS and SES-CD disease severity grouping before adjustment is 59% (241/411). FIG. 8B: Agreement between CDEIS and SES-CD disease severity groupings after application of linear regression equation increases to 80% (328/411). The ovals in the 2 tables indicate the samples in agreement. The table on the right shows the linear regression equation for conversion of SES-CD scores to CDEIS.

DETAILED DESCRIPTION

I. Introduction

Figure 1:
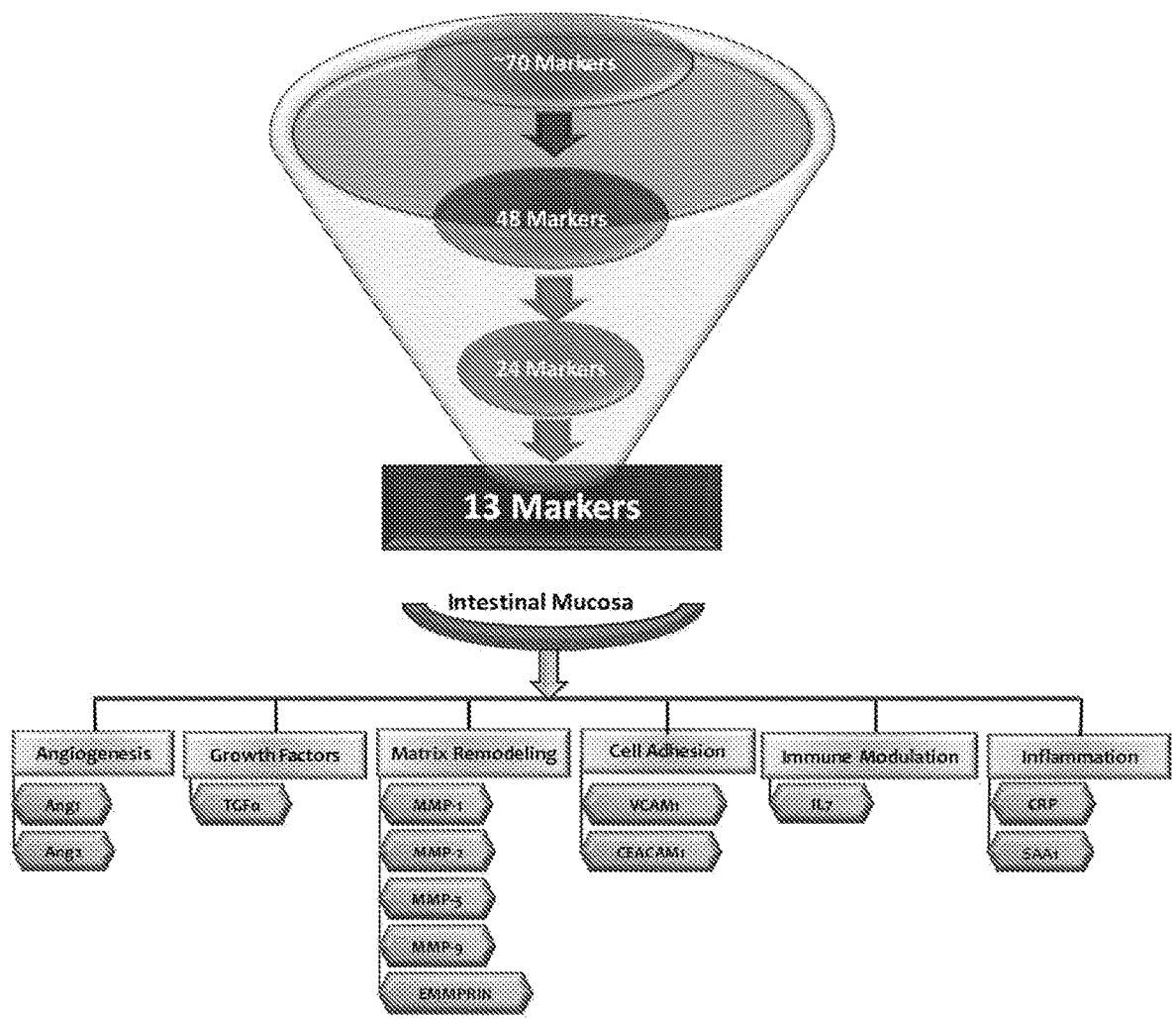
FIG. 1 shows that marker selection for the mucosal healing (MH) test was an iterative process that involved correlating the marker expression against visualized endoscopic disease severity. Markers from multiple signaling pathways were considered. The final model included 13 markers that represent 6 broad biological categories known to be involved in maintaining mucosal homeostasis. Note that the final model includes markers that are not simply limited to inflammatory markers. Ang 1, 2, Angiotensin 1, 2; TGFα, Transforming Growth Factor alpha; MMP 1, 2, 3 & 9, Matrix Metalloproteinase 1, 2, 3, & 9; EMMPRIN, Extracellular Matrix Metalloproteinase Inducer; VCAM, Vascular Cell Adhesion Molecule; CEACAM, Carcinoembryonic Antigen-related Cell Adhesion Molecule; IL-7, Interleukin-7; CRP, C-Reactive Protein; SAA1, Serum Amyloid A1.
Figure 2A:
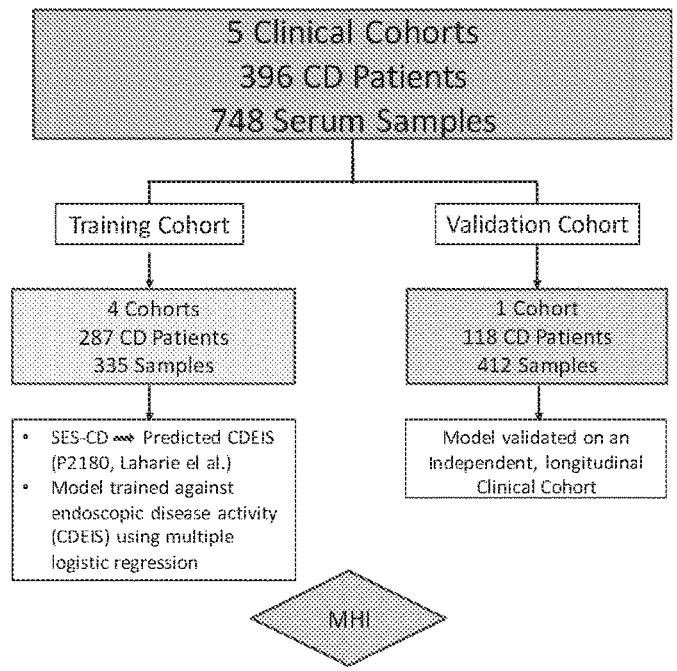
Figure 2B:
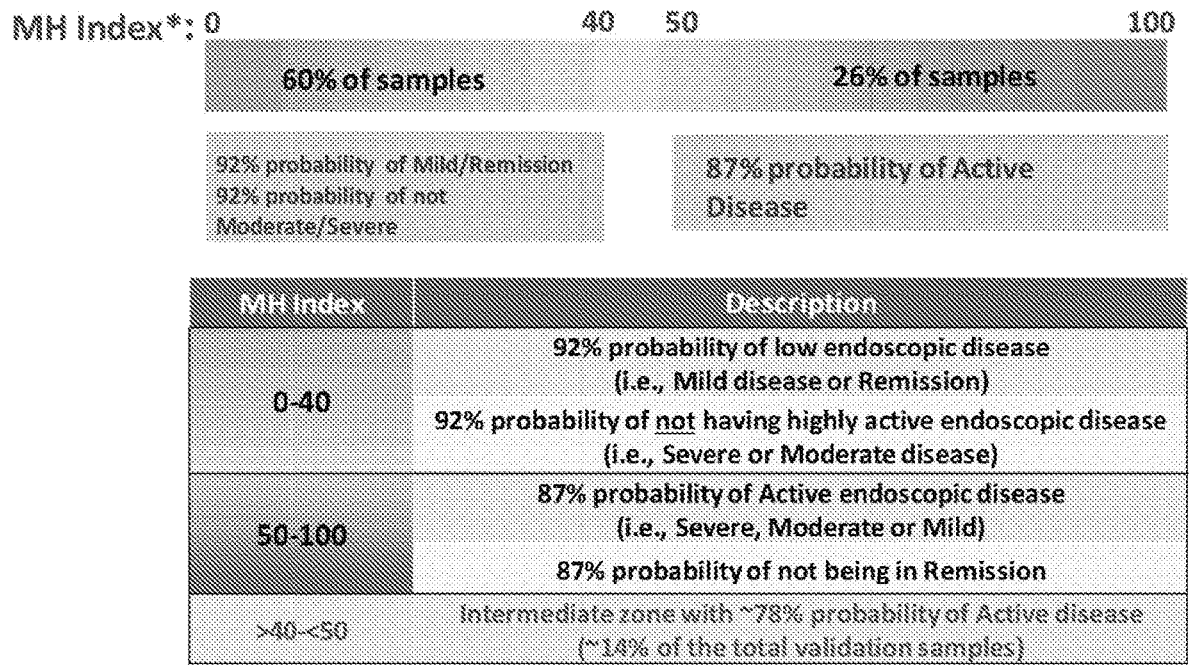

In general, provided herein are methods and kits for the non-invasive and accurate serological diagnostic testing of CD patients. The discovered proteomics-based test has surprisingly and advantageously been found to be an effective surrogate for assessing the intestinal mucosal state in CD patients. The diagnostic testing can be used regardless of the treatment type being used, and can address a need for everyday clinical patient management by predicting endoscopic appearance and MH with good accuracy. The provided methods and kits involve serum-based, multi-analyte MH algorithms that incorporate a panel of biomarkers associated with biological pathways important for the maintenance of mucosal homeostasis in CD patients. Using these algorithms, a peripheral blood-based test has been developed that can be used as a non-invasive surrogate for mucosal endoscopic activity assessed via ileocolonoscopy in CD patients. The incorporation of this test into current practice can aid in the management of CD patients and assist in determining therapeutic efficacy in a treat-to-target paradigm. In this way, the provided methods and kits can advantageously improve patient related outcomes and compliance to prescribed therapies.

II. Definitions

As used herein, the following terms have the meanings ascribed to them unless specified otherwise.

The term "mucosal healing" as used herein refers to restoration of normal mucosal appearance of a previously inflamed region, and complete or substantial absence of ulceration and inflammation at the endoscopic and microscopic levels. Mucosal healing includes repair and restoration of the mucosa, submucosa, and muscularis layers. Mucosal healing can also include neuronal and lymphangiogenic elements of the intestinal wall.

The terms "Mucosal Healing Index" and "MHI" as used herein refer to an empirically derived index that is derived based on an analysis of relevant biomarkers. In one aspect, the measured concentrations of the biomarkers are transformed into the index by an algorithm resident on a computer. In certain aspects, the index is a synthetic or human derived output, score, or cut off value(s), which express the biological data in numerical terms. The index can be used to determine or make or aid in making a clinical decision. A Mucosal Healing Index can be measured multiple instances over the course of time. In one aspect, the algorithm can be trained with known samples and thereafter validated with samples of known identity.

The terms "marker" and "biomarker" as used herein include any biochemical markers, serological markers, protein markers, genetic markers, analytes, and/or other clinical or echographic characteristics, that can be measured in a sample. In certain embodiments, a marker can be used to detect mucosal healing in a sample from an individual with a disease such as IBD including CD and ulcerative colitis.

The term "analyte" as used herein includes any molecule of interest, typically a macromolecule such as a polypeptide, whose presence, amount, and/or identity is determined. In certain instances, the analyte, either alone or in combination with one or more other analytes, is a marker for a disease state.

The term "sample" as used herein includes any biological specimen obtained from a subject or patient. Samples include, without limitation, whole blood, plasma, serum, red blood cells, white blood cells (e.g., peripheral blood mononuclear cells (PBMC), polymorphonuclear (PMN) cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample such as a biopsy of a site of inflammation (e.g., needle biopsy), and cellular extracts thereof.

The terms "subject," "patient," or "individual" as used herein refer to humans, but also to other animals including, e.g., other primates, rodents, canines, felines, equines, ovines, porcines, and the like.

The terms "statistical analysis", "statistical algorithm", and "statistical process" as used herein include any of a variety of methods and models used to determine relationships between variables.

III. Description of Exemplary Embodiments

In one embodiment, a method for assessing mucosal healing in a patient with CD is disclosed. The method includes providing a sample from a patient. In some embodiments, the sample is a serum sample. The method further includes detecting in the sample the expression levels of biomarkers generally known in the art to be associated with biological pathways important for the maintenance of mucosal homeostasis in CD patients. In some embodiments, the biomarkers include one or more angiopoietins such as Ang1 or Ang2. In some embodiments, the biomarkers include one or more adhesion proteins such as CEACAM1 or VCAM1. In some embodiments, the biomarkers include one or more growth factors such as TGFα. In some embodiments, the biomarkers include one or more inflammation response proteins such as CRP. In some embodiments, the biomarkers include one or more apolipoproteins such as SAA1, In some embodiments, the biomarkers include one or more matrix metalloproteinases and related inducers such as MMP-1, MMP-2, MMP-3, MMP-9, or EMMPRIN. In some embodiments, the biomarkers include one or more cytokines such as IL-7.

In certain aspects, the method includes detecting in the serum sample an expression level of each of two of more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. The two or more biomarkers can include, for example, Ang1 and Ang2, Ang1 and CEACAM1, Ang1 and VCAM1, Ang1 and TGFα, Ang1 and CRP, Ang1 and SAA1, Ang1 and MMP-1, Ang1 and MMP-2, Ang1 and MMP-3, Ang1 and MMP-9, Ang1 and EMMPRIN, or Ang1 and IL-7. The two or more biomarkers can include Ang2 and CEACAM1, Ang2 and VCAM1, Ang2 and TGFα, Ang2 and CRP, Ang2 and SAA1, Ang2 and MMP-1, Ang2 and MMP-2, Ang2 and MMP-3, Ang2 and MMP-9, Ang2 and EMMPRIN, or Ang2 and IL-7. The two or more biomarkers can include CEACAM1 and VCAM1, CEACAM1 and TGFα, CEACAM1 and CRP, CEACAM1 and SAA1, CEACAM1 and MMP-1, CEACAM1 and MMP-2, CEACAM1 and MMP-3, CEACAM1 and MMP-9, CEACAM1 and EMMPRIN, or CEACAM1 and IL-7. The two or more biomarkers can include VCAM1 and TGFα, VCAM1 and CRP, VCAM1 and SAA1, VCAM1 and MMP-1, VCAM1 and MMP-2, VCAM1 and MMP-3, VCAM1 and MMP-9, VCAM1 and EMMPRIN, or VCAM1 and IL-7. The two or more biomarkers can include TGFα and CRP, TGFα and SAA1, TGFα and MMP-1, TGFα and MMP-2, TGFα and MMP-3, TGFα and MMP-9, TGFα and EMMPRIN, or TGFα and IL-7. The two or more biomarkers can include CRP and SAA1, CRP and MMP-1, CRP and MMP-2, CRP and MMP-3, CRP and MMP-9, CRP and EMMPRIN, or CRP and IL-7. The two or more biomarkers can include SAA1 and MMP-1, SAA1 and MMP-2, SAA1 and MMP-3, SAA1 and MMP-9, SAA1 and EMMPRIN, or SAA1 and IL-7. The two or more biomarkers can include MMP-1 and MMP-2, MMP-1 and MMP-3, MMP-1 and MMP-9, MMP-1 and EMMPRIN, or MMP-1 and IL-7. The two or more biomarkers can include MMP-2 and MMP-3, MMP-2 and MMP-9, MMP-2 and EMMPRIN, or MMP-2 and IL-7. The two or more biomarkers can include MMP-3 and MMP-9, MMP-3 and EMMPRIN, or MMP-3 and IL-7. The two or more biomarkers can include MMP-9 and EMMPRIN, or MMP-9 and IL-7. The two or more biomarkers can include EMMPRIN and IL-7.

In certain aspects, the method includes detecting in the serum sample an expression level of each of three or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the method includes detecting in the serum sample an expression level of each of four or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the method includes detecting in the serum sample an expression level of each of five or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the method includes detecting in the serum sample an expression level of each of six or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the method includes detecting in the serum sample an expression level of each of seven or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the method includes detecting in the serum sample an expression level of each of eight or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the method includes detecting in the serum sample an expression level of each of nine or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the method includes detecting in the serum sample an expression level of each of ten or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the method includes detecting in the serum sample an expression level of each of eleven or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the method includes detecting in the serum sample an expression level of each of twelve or more biomarkers selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the method includes detecting in the serum sample an expression level of each of Ang1, Ang2, CEACAM1, VCAM1, TGFα, CRP, SAA1, MMP-1, MMP-2, MMP-3, MMP-9, EMMPRIN, and IL-7. In certain aspects, the method includes detecting in the serum sample one or more additional biomarkers generally known in the art to be associated with biological pathways important for the maintenance of mucosal homeostasis in CD patients.

In certain aspects, the expression levels of one or more biomarkers or analytes are measured in terms of mRNA expression with an assay such as, for example, a hybridization assay or an amplification-based assay. In some embodiments, the expression levels of one or more biomarkers or analytes are measured in terms of protein expression using, for example, an immunoassay (e.g., enzyme-linked immunosorbent assay (ELISA) or collaborative enzyme enhanced reactive immunoassay (CEER)), a homogeneous mobility shift assay (HMSA), or an immunohistochemical assay. Suitable ELISA kits for determining the presence or level of a growth factor, an inflammatory marker, or an anti-inflammatory marker in a serum, plasma, saliva, or urine sample are available from, e.g., Antigenix America Inc. (Huntington Station, N.Y.), Promega (Madison, Wis.), R&D Systems, Inc. (Minneapolis, Minn.), Invitrogen (Camarillo, Calif.), CHEMICON International, Inc. (Temecula, Calif.), Neogen Corp. (Lexington, Ky.), PeproTech (Rocky Hill, N.J.), Alpco Diagnostics (Salem, N.H.), Pierce Biotechnology, Inc. (Rockford, Ill.), and/or Abazyme (Needham, Mass.). CEER is described in the following patent documents, each of which are herein incorporated by reference in their entirety for all purposes: International Patent Application Publication Nos. WO 2008/036802, WO 2009/012140, WO 2009/108637, WO 2010/132723, WO 2011/008990, WO 2011/050069, WO 2012/088337, WO 2012/119113, and WO 2013/033623.

The provided methods further include applying a mathematical algorithm to the expression levels of the biomarkers, thereby producing a Mucosal Healing Index (MHI) score for the patient. In some embodiments, the MHI score has a scale from 0 to 100. In certain aspects, the mathematical algorithm includes one or more equations relating measured expression levels of the biomarkers to an endoscopic scoring index. The mathematical algorithm can include, for example, two or more equations, three or more equations, four or more equations, five or more equations, six or more equations, seven or more equations, eight or more equations, nine or more equations, or ten or more equations. The equations can relate to raw data of biomarker expression levels, or to transformed data of the expression levels. In some embodiments, the equations relate to the natural logarithms of the biomarker expression levels.

The biomarker expression levels can be related to an endoscopic scoring index such as the Crohn's Disease Endoscopic Index of Severity (CDEIS) or the Simple Endoscopic Score for Crohn's Disease (SES-CD). CDEIS and SES-CD are each generally accepted endoscopic scoring indices conventionally used as standards to assess the state of mucosal disease in CD patients, score mucosal status, and determine the outcome of clinical trials that utilize mucosal healing as an endpoint. In certain aspects, the equations of the mathematical algorithm relate the measured biomarker expression levels of a patient to the predicted CDEIS of the patient. In certain aspects, the equations relate the measured biomarker expression levels of a patient to the predicted SES-CD of the patent. In some embodiments, a CDEIS value is converted to an SES-CD value. In some embodiments, an SES-CD value is converted to a CDEIS value. Although a linear offset between CDEIS and SES-CD is widely accepted, the provided methods can use a variety of statistical processes for converting scores of one index to another.

The relationships between the biomarker expression levels and the endoscopic scoring index, mucosal healing index and diagnostic prediction can be derived by any of a number of statistical processes or statistical analysis techniques. In some embodiments, logistic regression is used to derive one or more equations of the mathematical algorithm. In some embodiments, linear regression is used to derive one or more equations of the algorithm. In some embodiments, ordinary least squares regression or unconditional logistic regression is used to derive one or more equations of the algorithm.

In some embodiments, the statistical analyses includes a quantile measurement of one or more biomarkers. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The algorithm can also include the use of percentile ranges of marker levels (e.g., tertiles, quartile, quintiles, etc.), or their cumulative indices (e.g., quartile sums of marker levels to obtain quartile sum scores (QSS), etc.) as variables in the statistical analyses (just as with continuous variables).

In some embodiments, the statistical analyses include one or more learning statistical classifier systems. As used herein, the term "learning statistical classifier system" includes a machine learning algorithmic technique capable of adapting to complex data sets (e.g., panel of markers of interest) and making decisions based upon such data sets. In some embodiments, a single learning statistical classifier system such as a decision/classification tree (e.g., random forest (RF) or classification and regression tree (C&RT)) is used. In some embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as RF, C&RT, boosted trees, etc.), Probably Approximately Correct (PAC) learning, connectionist learning (e.g., neural networks (NN), artificial neural networks (ANN), neuro fuzzy networks (NFN), network structures, the Cox Proportional-Hazards Model (CPHM), perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, Machine Learning, 45:5-32 (2001); and http://stat-www.berkeley.edu/users/breiman/RandomForests/cc home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the C&RT software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADA-LINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the $SVM_{light}$ software developed by Thorsten Joachims (Cornell University) or using the LIBSVM software developed by Chih-Chung Chang and Chih-Jen Lin (National Taiwan University).

The various statistical methods and models described herein can be trained and tested using a cohort of samples (e.g., serological samples) from healthy, IBD, or non-IBD individuals. The equations of the mathematical algorithm can be trained using, for example, clinical data from one or more cross-sectional studies, e.g., studies including a different patient sample at each surveyed time point. The equations of the mathematical algorithm can be trained using clinical data from one or more longitudinal studies, e.g., studies including the same patient sample across multiple surveyed time points. In certain aspects, one or more equations of the mathematical algorithm are trained using cross-sectional data and one or more equations of the mathematical algorithm are trained using longitudinal data. The equations of the mathematical algorithm can be validated using, for example, clinical data from one or more cross-sectional studies. The equations of the mathematical algorithm can be validated using clinical data from one or more longitudinal studies. In certain aspects, one or more equations of the mathematical algorithm are validated using cross-sectional data and one or more equations of the mathematical algorithm are validated using longitudinal data.

In certain aspects, one or more equations of the mathematical algorithm are derived to model diagnostic sensitivity, e.g., the proportion of actual positives that are correctly identified as such. For example, one or more equations can be trained using the data to predict an active disease diagnosis versus a remission diagnosis with the measured biomarker expression levels. In certain aspects, one or more equations of the mathematical algorithm are derived to model diagnostic specificity, e.g., the proportion of actual negatives that are correctly identified as such. For example, one or more equations can be trained using the data to predict a mild disease or remission diagnosis versus a severe disease or moderate disease diagnosis with the measured biomarker expression levels. In some embodiments, the mathematical algorithm includes two or more equations, one or more of which are derived to model diagnostic sensitivity, and one or more of which are derived to model diagnostic specificity. In certain aspects, the mathematical algorithm applies one or more diagnostic sensitivity equations prior to applying one or more diagnostic specificity equations in a sequence to generate an MHI score or value. In certain aspects, the mathematical algorithm applies one or more diagnostic specificity equations prior to applying one or more diagnostic sensitivity equations in a sequence to generate an MHI score or value.

In certain aspects, the method further includes determining that the patient has a high probability of being in remission or having mild endoscopic disease when the MHI score is less than or equal to 40. In some embodiments, a diagnosis of remission corresponds to a CDEIS of less than 3. In some embodiments, a diagnosis of mild endoscopic disease corresponds to a CDEIS between 3 and 8. The high probability of a patient with an MHI score less than or equal to 40 being in remission of having mild endoscopic disease (e.g., having a CDEIS less than 8) can be, for example between 83% and 98%, e.g., between 83% and 92%, between 84.5% and 93.5%, between 86% and 95%, between 87.5% and 96.5%, or between 89% and 98%. In terms of lower limits, the high probability that a patient with and MHI score less than or equal to 40 is in remission or has mild endoscopic disease can be greater than or equal to 83%, e.g., greater than or equal to 84.5%, greater than or equal to 86%, greater than or equal to 87.5%, greater than or equal to 89%, greater than or equal to 90.5%, greater than or equal to 92%, greater than or equal to 93.5%, greater than or equal to 95%, or greater than or equal to 96.5%. Higher probabilities, e.g., greater than or equal to 98%, are also contemplated.

In certain aspects, the method further includes determining that the patient has a high probability of having endoscopically active disease when the MHI score is greater than or equal to 50. In some embodiments, a diagnosis of endoscopically active disease corresponds to a CDEIS of greater than or equal to 3. The high probability of a patient with an MHI score greater than or equal to 50 having endoscopically active disease can be, for example, between 80% and 95%, e.g., between 80% and 89%, between 81.5% and 90.5%, between 83% and 92%, between 84.5% and 93.5%, or between 86% and 95%. In terms of lower limits, the high probability of a patient with an MHI score greater than or equal to 50 having endoscopically active disease can be greater than or equal to 80%, e.g., greater than or equal to 81.5%, greater than or equal to 83%, greater than or equal to 84.5%, greater than or equal to 86%, greater than or equal to 87.5%, greater than or equal to 89%, greater than or equal to 90.5%, greater than or equal to 92%, or greater than or equal to 93.5%. Higher probabilities, e.g., greater than or equal to 95%, are also contemplated.

In certain aspects, the method further includes determining that the patient has a moderate probability of having endoscopically active disease when the MHI score is between 40 and 50. The moderate probability of a patient with an MHI score between 40 and 50 having endoscopically active disease can be, for example, between 70% and 85%, e.g., between 70% and 79%, between 71.5% and 80.5%, between 73% and 82%, between 74.5% and 83.5%, or between 76% and 85%. In terms of lower limits, the moderate probability of a patient with an MHI score between 40 and 50 having endoscopically active disease can be greater than or equal to 70%, e.g., greater than or equal to 71.5%, greater than or equal to 73%, greater than or equal to 74.5%, greater than or equal to 76%, greater than or equal to 77.5%, greater than or equal to 79%, greater than or equal to 80.5%, greater than or equal to 82%, or greater than or equal to 83.5%. Higher probabilities, e.g., greater than or equal to 85%, are also contemplated.

The disclosed methods provide non-invasive tools for predicting the likelihood of mucosal healing and/or monitoring mucosal healing in patients, such as patients receiving biologic or non-biologic therapy. In addition, the present disclosure provides methods of determining or evaluating the efficacy of the therapy, and predicting therapeutic response, risk of relapse, and risk of surgery in patients based upon the progression of mucosal healing in the subject. In particular, the methods of the present disclosure find utility for selecting a therapy for continued treatment, for determining when or how to adjust or modify (e.g., increase or decrease) subsequent therapeutic agent doses to optimize therapeutic efficacy and/or to reduce toxicity, and/or for determining when or how to change the current course of therapy (e.g., switch to a different drug or to a drug that targets a different mechanism). The disclosed methods also can be used to assess mucosal healing at colonic, ileocolonic, and/or ileal disease locations in the patient, and to assess mucosal healing in the patient after surgery, such as by identifying post-operative, endoscopic recurrence in the patient.

The therapy can include the administration of therapeutic agents with a suitable pharmaceutical excipient as necessary and can be carried out via any of the accepted modes of administration. Suitable therapeutic agents for use with the disclosed methods include, but are not limited to, biologic agents such as antibodies, conventional drugs, nutritional supplements, and combinations thereof. Administration can be, for example, intravenous, topical, subcutaneous, transcutaneous, transdermal, intramuscular, oral, buccal, sublingual, gingival, palatal, intra joint, parenteral, intra-arteriole, intradermal, intraventricular, intracranial, intraperitoneal, intralesional, intranasal, rectal, vaginal, or by inhalation. A therapeutic agent can be administered at the same time, just prior to, or just after the administration of a second drug (e.g., a second therapeutic agent, a drug useful for reducing the side-effects of the first therapeutic agent, etc.).

A therapeutically effective amount of a therapeutic agent can be administered repeatedly, e.g., at least 2, 3, 4, 5, 6, 7, 8, or more times, or the dose can be administered by continuous infusion. The dose can take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

The therapeutic agent can be administered in physically discrete units suitable as unitary dosages for human subjects and other mammals, each unit containing a predetermined quantity of a therapeutic agent calculated to produce the desired onset, tolerability, and/or therapeutic effects, in association with a suitable pharmaceutical excipient (e.g., an ampoule). In addition, more concentrated dosage forms can be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the therapeutic agent.

Methods for preparing such dosage forms are known to those skilled in the art (see, e.g., *Remington's Pharmaceutical Sciences,* 18th Ed., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., Remington's Pharmaceutical Sciences, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms can also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with a therapeutic agent, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. A therapeutic agent can also be formulated into a suppository disposed, for example, in a polyethylene glycol (PEG) carrier.

Liquid dosage forms can be prepared by dissolving or dispersing a therapeutic agent and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. A therapeutic agent can also be formulated into a retention enema.

For topical administration, the therapeutically effective dose can be in the form of emulsions, lotions, gels, foams, creams, jellies, solutions, suspensions, ointments, and transdermal patches. For administration by inhalation, a therapeutic agent can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

As used herein, the term "therapeutic agent" includes all pharmaceutically acceptable forms of a drug that is useful for treating one or more symptoms associated with CD. For example, the therapeutic agent can be in a racemic or isomeric mixture, a solid complex bound to an ion exchange resin, or the like. In addition, the therapeutic agent can be in a solvated form. The term is also intended to include all pharmaceutically acceptable salts, derivatives, and analogs of the therapeutic agent being described, as well as combinations thereof. For example, the pharmaceutically acceptable salts of a therapeutic agent include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of a therapeutic agent is suitable for use in the methods of the present invention, e.g., a pharmaceutically acceptable salt of a therapeutic agent, a free base of a therapeutic agent, or a mixture thereof.

Biologic agents include, e.g., anti-cytokine and chemokine antibodies such as anti-tumor necrosis factor alpha (TNFα) antibodies. Non-limiting examples of anti-TNFα antibodies include: chimeric monoclonal antibodies such as infliximab (Remicade®) (Centocor, Inc.; Horsham, Pa.), which is a chimeric IgG1 anti-TNFα monoclonal antibody; humanized monoclonal antibodies such as CDP571 and the PEGylated CDP870; fully human monoclonal antibodies such as adalimumab (Humira®) (Abbott Laboratories; Abbott Park, Ill.); p75 fusion proteins such as etanercept (Enbrel®) (Amgen; Thousand Oaks, Calif.; Wyeth Pharmaceuticals Inc.; Collegeville, Pa.); small molecules (e.g., MAP kinase inhibitors); and combinations thereof. See, Ghosh, Novartis Found Symp., 263:193-205 (2004).

Other biologic agents include, e.g., anti-cell adhesion antibodies such as natalizumab (Tysabri®) (Elan Pharmaceuticals, Inc.; Dublin, Ireland; Biogen Idec; Cambridge, Mass.), which is a humanized monoclonal antibody against the cellular adhesion molecule α4-integrin, and MLN-02 (Millennium Pharmaceuticals; Cambridge, Mass.), which is a humanized IgG1 anti-α4β7-integrin monoclonal antibody; anti-T cell agents; anti-CD3 antibodies such as visilizumab (Nuvion®) (PDL BioPharma; Incline Village, Nev.), which is a humanized IgG2M3 anti-CD3 monoclonal antibody; anti-CD4 antibodies such as priliximab (cM-T412) (Centocor, Inc.; Horsham, Pa.), which is a chimeric anti-CD4 monoclonal antibody; anti-IL-2 receptor alpha (CD25) antibodies such as daclizumab Zenapax®) (PDL BioPharma; Incline Village, Nev.; Roche; Nutley, N.J.), which is a humanized IgG1 anti-CD25 monoclonal antibody; basiliximab (Simulect®) (Novartis; Basel, Switzerland), which is a chimeric IgG1 anti-CD25 monoclonal antibody; vedolizumab (Entyvio®) (Millennium Pharmaceuticals), which is a humanized antibody against integrin α4β7; ustekinumab (Stelara®) (Centocor), which is a humanized antibody against IL-12 and IL-23; and combinations thereof.

Examples of conventional drugs include, without limitation, aminosalicylates (e.g., mesalazine, sulfasalazine, and the like), corticosteroids (e.g., prednisone), thiopurines (e.g., azathioprine, 6-mercaptopurine, and the like), methotrexate, free bases thereof, pharmaceutically acceptable salts thereof, derivatives thereof, analogs thereof, and combinations thereof.

Also disclosed herein are kits that include two or more binding partners. Each of the two or more binding partners is attached to one or more solid supports, and each of the two or more binding partners is capable of binding a different analyte selected from the group consisting of Ang1, Ang2, CEACAM1, VCAM1, TGFα, CRP, SAA1, MMP-1, MMP-2, MMP-3, MMP-9, EMMPRIN, and IL-7. The two or more binding partners can bind, for example, Ang1 and Ang2, Ang1 and CEACAM1, Ang1 and VCAM1, Ang1 and TGFα, Ang1 and CRP, Ang1 and SAA1, Ang1 and MMP-1, Ang1 and MMP-2, Ang1 and MMP-3, Ang1 and MMP-9, Ang1 and EMMPRIN, or Ang1 and IL-7. The two or more binding partners can bind Ang2 and CEACAM1, Ang2 and VCAM1, Ang2 and TGFα, Ang2 and CRP, Ang2 and SAA1, Ang2 and MMP-1, Ang2 and MMP-2, Ang2 and MMP-3, Ang2 and MMP-9, Ang2 and EMMPRIN, or Ang2 and IL-7. The two or more binding partners can bind CEACAM1 and VCAM1, CEACAM1 and TGFα, CEACAM1 and CRP, CEACAM1 and SAA1, CEACAM1 and MMP-1, CEACAM1 and MMP-2, CEACAM1 and MMP-3, CEACAM1 and MMP-9, CEACAM1 and EMMPRIN, or CEACAM1 and IL-7. The two or more binding partners can bind VCAM1 and TGFα, VCAM1 and CRP, VCAM1 and SAA1, VCAM1 and MMP-1, VCAM1 and MMP-2, VCAM1 and MMP-3, VCAM1 and MMP-9, VCAM1 and EMMPRIN, or VCAM1 and IL-7. The two or more binding partners can bind TGFα and CRP, TGFα and SAA1, TGFα and MMP-1, TGFα and MMP-2, TGFα and MMP-3, TGFα and MMP-9, TGFα and EMMPRIN, or TGFα and IL-7. The two or more binding partners can bind CRP and SAA1, CRP and MMP-1, CRP and MMP-2, CRP and MMP-3, CRP and MMP-9, CRP and EMMPRIN, or CRP and IL-7. The two or more binding partners can bind SAA1 and MMP-1, SAA1 and MMP-2, SAA1 and MMP-3, SAA1 and MMP-9, SAA1 and EMMPRIN, or SAA1 and IL-7. The two or more binding partners can bind MMP-1 and MMP-2, MMP-1 and MMP-3, MMP-1 and MMP-9, MMP-1 and EMMPRIN, or MMP-1 and IL-7. The two or more binding partners can bind MMP-2 and MMP-3, MMP-2 and MMP-9, MMP-2 and EMMPRIN, or MMP-2 and IL-7. The two or more binding partners can bind MMP-3 and MMP-9, MMP-3 and EMMPRIN, or MMP-3 and IL-7. The two or more binding partners can bind MMP-9 and EMMPRIN, or MMP-9 and IL-7. The two or more binding partners can bind EMMPRIN and IL-7.

In certain aspects, the kit includes binding partners for each of three or more analytes selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the kit includes binding partners for each of four or more analytes selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the kit includes binding partners for each of five or more analytes selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the kit includes binding partners for each of six or more analytes selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the kit includes binding partners for each of seven or more analytes selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the kit includes binding partners for each of eight or more analytes selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the kit includes binding partners for each of nine or more analytes selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the kit includes binding partners for each of ten or more analytes selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the kit includes binding partners for each of eleven or more analytes selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the kit includes binding partners for each of twelve or more analytes selected from the group consisting of Ang1, Ang2, CEACAM1, VCAM1, TGFα, CRP, SAA1, MMP-1, MMP-2, MMP-3, MMP-9, EMMPRIN, and IL-7. In certain aspects, the kit includes binding partners for each of Ang1, Ang2, CEACAM1, VCAM1, TGFα, CRP, SAA1, MMP-1, MMP-2, MMP-3, MMP-9, EMMPRIN, and IL-7. In certain aspects, the kit includes binding partners for one or more additional analytes generally known in the art to be associated with biological pathways important for the maintenance of mucosal homeostasis in CD patients.

In some embodiments, one or more of the binding partners are antibodies. In certain aspects, the antibodies can be used to detect analytes of interest in a multiplex, high-throughput single-detection (i.e., two-antibody) assay. As a non-limiting example, the two antibodies used in the assay can include: (1) a capture antibody specific for the analyte; and (2) a detection antibody specific for an activated form of the analyte (i.e., activation state-dependent antibody). The activation state-dependent antibody is capable of detecting, for example, the phosphorylation, ubiquitination, and/or complexation state of the analyte. Alternatively, the detection antibody includes an activation state-independent antibody, which detects the total amount of the analyte in the sample. The activation state-independent antibody is generally capable of detecting both the activated and non-activated forms of the analyte.

In certain aspects one or more of the binding partners are antibodies that can be used to detect analytes of interest in a multiplex, high-throughput proximity (i.e., three-antibody) assay. As a non-limiting example, the three antibodies used in the proximity assay can include: (1) a capture antibody specific for the analyte; (2) a detection antibody specific for an activated form of the analyte (i.e., activation state-dependent antibody); and (3) a detection antibody which detects the total amount of the analyte (i.e., activation state-independent antibody). The activation state-dependent antibody is capable of detecting, for example, the phosphorylation, ubiquitination, and/or complexation state of the analyte. The activation state-dependent antibody is generally capable of detecting both the activated and non-activated forms of the analyte.

One skilled in the art will appreciate that binding partners other than antibodies can be used with the provided kits to immobilize and/or detect one or more analytes in the patient sample. Non-limiting examples of such binding partners include ligands or receptors of the analyte, substrates of the analyte, binding domains (e.g., PTB, SH2, etc.), aptamers, and the like.

In certain aspects, the binding of the analyte by the binding partner can include an ionic interaction. In certain aspects, the binding of the analyte by the binding partner can include a non-ionic interaction. In certain aspects, the binding of the analyte by the binding partner can include a covalent interaction.

The one or more solid supports of the kit can include, for example, glass (e.g., a glass slide), plastic, chips, pins, filters, beads (e.g., magnetic beads, polystyrene beads, etc.), paper, membranes (e.g., nylon, nitrocellulose, PVDF, etc.), fiber bundles, gels, metals, ceramics, or any other suitable substrate. In some embodiments, the two or more binding partners are covalently attached to the one or more solid supports.

In some embodiments, the binding partners are attached to beads. In certain aspects, each category of binding partner included in the kit is attached to a different bead type to enable multiplex assays. For example, each binding partner category can be attached to a bead having distinct properties, such as color, that can be distinguished using lasers, light emitting diodes (LEDs), digital signal processors, photo detectors, charge-coupled device (CCD) imagers, or other equipment. Examples of solid supports suitable for use with the provided kits and methods include LUMINEX® beads, available from Luminex Corporation (Austin, Tex.).

In certain aspects, the kits further include instructions for methods of using the kit to assess mucosal healing in a patient with CD. The instructions can be for any of the method steps described above. For example, the kit instructions can be for contacting the one or more solid supports with a serum sample from a patient. The kit instructions can be for detecting in the serum sample an expression level of each of the analytes bound by the one or more binding partners. The kit instructions can be for applying a mathematical algorithm to the expression levels of the analytes, thereby producing an MHI score for the patient. In certain aspects, the MHI score has a scale from 0 to 100. The kit instructions can be for determining that the patient has a high probability of being in remission or having mild endoscopic disease when the MHI score is less than or equal to 40. The kit instructions can be for determining that the patient has a high probability of having endoscopically active disease when the MHI score is greater than or equal to 50. The kit instructions can be for determining that the patient has a moderate probability of having endoscopically active disease when the MHI score is between 40 and 50.

The kits can further include additional reagents useful for performing the specific methods of the present disclosure. The kits can include, for example, assay substrates, standards, diluents, biotin-antibodies, wash buffers, capture/release reagents, or combinations thereof.

IV. Examples

The following examples are offered for illustrative purposes, and are not intended to limit the disclosure in any manner. Those of skill in the art will readily recognize a variety of non-critical parameters which can be changed or modified to yield essentially the same results.

Example 1: Development of a Mathematical Algorithm Relating Serum Analyte Levels to Diagnostic Assessments A clinical data set including serum analyte expression levels and SES-CD scores is provided. Natural logarithm transformations are applied to expression levels of two or more serum analytes, e.g., biomarkers, to reduce data skewness and generate a Gaussian distribution. Maximum likelihood estimates (MLE) are used to produce a correlation matrix between the transformed serum analyte expression levels. Linear regression is used to convert SES-CD values to CDEIS values, and simple linear/logistic regression analysis is used to test the association between CDEIS binary endpoints and biomarker expression levels. Stepwise linear/logistic regression using backward elimination with Akaike Information Criterion (AIC) is then used to fit biomarkers to CDEIS binary outcomes.

The provided clinical data is divided into a model algorithm training set and a model algorithm validation set. The model training set includes cross-sectional samples to minimize bias from repeated measurements, and the validation set includes longitudinal samples to explore the use of the algorithm as a patient monitoring tool. One model is trained using data for active disease versus remission as CDEIS binary outcomes, and one model is trained using data for moderate/severe disease versus remission/mild disease as CDEIS binary outcomes. The models are applied sequentially to create an MHI score within the continuous range from 0 to 100.

Example 2: Development and Validation of a Multi-Marker Serum Test for the Assessment of Mucosal Healing in Crohn's Disease Patients Retrospective serum samples taken from adult CD patients at or close to the time of ileocolonoscopy and a panel of serum proteomics biomarkers were used to train a logistic regression model against visualized endoscopic disease severity determined by either CDEIS or SES-CD scores. MH was defined as the absence of ulcers on endoscopy. The model was independently validated in a prospectively collected, centrally read, longitudinal cohort of 118 patients from the TAILORIX clinical trial. The final model utilized 13 biomarkers to produce a 0-100 scale termed the Mucosal Healing Index (MHI). The markers represent multiple biological pathways thought to be involved in the MH process including angiogenesis (Ang1, Ang2), cell adhesion (CEACAM1, VCAM1), growth factor signaling (TGFα), inflammation (CRP, SAA1), matrix remodeling (mmp-1, -2, -3, -9 and EMMPRIN), and immune modulation (IL7).

A total of 748 samples from 396 patients (mean age: 34 years, 49% males, 26% ileal, 52% ileocolonic and 22% colonic disease) were used for the training and validation of the MH test. The overall accuracy of the test was 90% with a negative predictive value (NPV) of 92% for identifying patients in remission (CDEIS <3) or with mild (CDEIS 3-8) endoscopic disease (MHI range 0-40) and a positive predictive value (PPV) of 87% for identifying patients with endoscopic evidence of active disease (CDEIS ≥3; MHI range 50-100). 14% of the specimens fell within an intermediate zone (MHI 41-49) with an observed 78% probability of active disease. Test performance is shown in Table 1.

TABLE 1

| | |
|---|---|
| Accuracy | 90% (95% CI: 87% to 93%) |
| Sensitivity | 82% (95% CI: 75% to 89%) |
| Specificity | 94% (95% CI: 91% to 97%) |
| PPV | 87% (95% CI: 80% to 93%) |
| NPV | 92% (95% CI: 88% to 95%) |

Example 3: Validation of a Non-Invasive, Serological Test to Assess the Efficacy of Biologic or Non-Biologic Therapies on Mucosal Health of Patients with Crohn's Disease This test was validated in a CD cohort of infliximab-treated patients. This study aims to validate the performance of this test in a cohort of patients with CD treated with either biologic or non-biologic therapeutic options (therapeutic agnostic). Cross-sectional specimens from patients with CD, enrolled at different centers and treated with different therapies, were collected at or close to endoscopic examination. Samples were evaluated using a serum test that utilizes the expression of 13 protein biomarkers modeled into a mathematical algorithm to produce a 0-100 scale termed as the Mucosal Healing Index (MHI). The biomarkers, that represent biological pathways involved in maintaining intestinal mucosal health, are Ang1, Ang2, CEACAM1, CRP, EMMPRIN, IL7, mmp-1, -2, -3, -9, SAA1, TGFα, and VCAM1. Data on endoscopic disease severity were determined by either CDEIS or SES-CD. MH was defined as the absence of ulcers on endoscopy.

Patient characteristics are shown in Table 2. Fifty percent of the cohort consisted of patients treated with biologic options. 42% of the remaining patients were anti-TNFα naïve or on therapy with thiopurines or mesalamine. Therapeutic information was unavailable for 22/278 patients (8%) which were excluded from the analysis. The overall test accuracy for determining presence of MH (i.e. efficacy of the drug) in this CD patient population was 90% (Table 3). The negative predictive value (NPV) was 89% for identifying patients in remission or with mild endoscopic disease. The positive predictive value (PPV) was 90% for identifying patients with endoscopic active disease (CDEIS>3). An intermediate zone, 16% of the specimens, showed a 79% probability of active disease.

TABLE 2

| Patient Characteristics | |
|---|---|
| Age [mean in years (SD)] | 38 (15) |
| Male gender [n (%)] | 122 (43.9) |
| On adalimumab [n (%)] | 51 (18.3) |
| On infliximab [n (%)] | 42 (15) |
| On vedolizumab [n (%)] | 27 (9.7) |
| On ustekinumab [n (%)] | 18 (6.5) |
| On certolizumab [n (%)] | 1 (0.4) |
| On natalizumab [n (%)] | 1 (0.4) |
| On non-biologics [n (%)] | 116 (41.7) |
| Endoscopic Disease Severity | |
| Severe [n (%)], (CDEIS: >12 or SES-CD: >15) | 49 (17.6) |
| Moderate [n (%)], (CDEIS: 9-12 or SES-CD: 7-15) | 33 (11.9) |
| Mild [n (%)], (CDEIS: 3-8 or SES-CD: 3-6) | 109 (39.2) |
| Remission (n (%)], (CDEIS: <3 or SES-CD: <3) | 87 (31.3) |

TABLE 3

| Overall MHI Test Performance for Detecting Endoscopically Visualized CD | |
|---|---|
| Accuracy | 90% (95% CI: 85% to 94%) |
| Sensitivity | 89% (95% CI: 81% to 94%) |
| Specificity | 91% (95% CI: 84% to 96%) |
| PPV | 90% (95% CI: 84% to 94%) |
| NPV | 89% (95% CI: 83% to 93%) |

These results demonstrate that performance of the test is similar regardless of the type of treatment employed. This test could be utilized as a non-invasive tool to monitor and manage the care of patients with CD.

Example 4: A Novel Serum Test to Describe the Mucosal Healing State by Location in Crohn's Disease Patients The aim of the present study was to compare the diagnostic performance of this novel serological test in specific subtypes of CD patients classified by the location of their disease in order to understand its clinical utility.

In the present study, validation performance of MHI, according to disease location, has been evaluated in 412 longitudinal specimens from 118 CD patients collected during the TAILORIX clinical trial. Specimens were collected from patients at the time of or close to endoscopy. Endoscopic scoring was centrally read and MH was defined as the absence of visual endoscopic ulcers. MHI test assay performance was assessed for sensitivity, specificity, positive predictive value (PPV), and negative predictive value (NPV) in the combined group and by each disease location.

Patient characteristics are shown in Table 4. Disease locations were classified according to the Montreal classification. Test accuracy was 87%, 90% and 95% for colonic, ileocolonic and ileal disease, respectively. The detailed performance across disease locations is shown in Table 5.

TABLE 4

Patient Characteristics

|  | Ileal (L1) | Colonic (L2) | Ileocolonic (L3) |
|---|---|---|---|
| Patients [n (%)] | 27 (22.9) | 20 (16.9) | 71 (60.2) |
| Age [mean in years (SD)] | 37 (16) | 41 (15) | 31 (12) |
| Male gender [n (%)] | 9 (33.3) | 7 (35) | 29 (40.8) |
| Active Disease at baseline [n (%)], (CDEIS: ≥3) | 26 (96.3) | 19 (95.0) | 69 (97.2) |

TABLE 5

Performance by Disease Location

| CD Location | Test Accuracy | Sensitivity | Specificity | PPV | NPV |
|---|---|---|---|---|---|
| All Patients (# samples: 412) | 90% (95% CI: ±87% to 93%) | 82% (95% CI: ±75% to 89%) | 94% (95% CI: ±91% to 97%) | 87% (95% CI: ±80% to 93%) | 92% (95% CI: ±88% to 95%) |
| Ileocolonic (# samples: 244) | 90% (95% CI: ±85% to 94%) | 80% (95% CI: ±69% to 89%) | 95% (95% CI: +90% to 98%) | 89% (95% CI: +80% to 94%) | 90% (95% CI: +85% to 94%) |
| Ileal (# samples: 96) | 95% (95% CI: ±88% to 99%) | 86% (95% CI: +65% to 97%) | 98% (95% CI: +91% to 100%) | 95% (95% CI: +73% to 99%) | 95% (95% CI: +87% to 98%) |
| Colonic (# samples: 72) | 87% (95% CI: ±77% to 94%) | 89% (95% CI: ±67% to 99%) | 86% (95% CI: ±73% to 95%) | 74% (95% CI: ±57% to 86%) | 95% (95% CI: ±84% to 99%) |

These results demonstrate that the novel serum test for the non-invasive evaluation of mucosal health shows comparable performance across ileal, ileocolonic and colonic anatomic disease locations in patients with CD. These results further validate the clinical utility of the test as a beneficial aid in assessing the state of the intestinal mucosa for CD patients regardless of disease location.

Example 5: The Effects of Different Scoring Indices for Evaluation of Crohn's Disease Activity Both CDEIS and SES-CD scores were collected at the same time by the same physician during a centrally read, prospectively collected, longitudinal cohort of 118 CD patients in the TAILORIX clinical trial. Up to 3 ileocolonoscopic scores were available from each patient over a period of 1 year. Standard endoscopic disease severity definitions were applied to both CDEIS and SES-CD scores obtained at each instance of endoscopy. CDEIS scores were classified as remission <3, mild 3-8, moderate 9-12, and severe >12. For SES-CD the same groups were defined as <3, 3-6, 7-15, and >15, respectively. The two indices were normalized using linear regression and contingency tables were created for both pre- and post-normalization for the categorical outcomes of those endpoints.

Using the raw CDEIS and SES-CD scores, a contingency table (Table 7; Non-adjusted Agreement) shows that the overall agreement in endoscopic disease severity states (Remission, Mild, Moderate and Severe) is only 59% (242/411). 33% ($^{58}/_{175}$) of the scores deemed as disease in remission by CDEIS are classified as active disease by SES-CD. Likewise, $^{81}/_{146}$ (~56%) of mild disease instances by CDEIS are suggested to have a disease at higher severity, i.e., moderate disease with SES-CD.

TABLE 6

Contingency tables pre- and post-normalization of CDEIS and SES-CD scores

| | | Non-Adjusted Agreement | | | | | | Normalized Agreement | | | |
|---|---|---|---|---|---|---|---|---|---|---|---|
| | | SES-CD | | | | | | Predicted CDEIS | | | |
| | | Severe | Moderate | Mild | Remission | | | Severe | Moderate | Mild | Remission |
| CDEIS | Severe | 44 | 6 | 1 | 1 | CDEIS | Severe | 37 | 8 | 6 | 0 |
| | Moderate | 15 | 24 | 0 | 0 | | Moderate | 11 | 15 | 13 | 0 |
| | Mild | 2 | 81 | 56 | 7 | | Mild | 1 | 7 | 119 | 19 |
| | Remission | 0 | 0 | 58 | 117 | | Remission | 0 | 0 | 18 | 157 |
| | Agreement = 44 + 24 + 56 + 117 = 241 | | | | | | Agreement = 37 + 15 + 119 + 157 = 328 | | | | |
| | Total = 411 | | | | | | Total = 411 | | | | |

After applying the observed linear regression equation (CDEIS=0.25+0.69*SESCD; r=0.92) to normalize the two scores the overall agreement improves to 80% (Table 6; Normalized Agreement).

Although CDEIS and SES-CD scores correlate well and are often considered as endoscopic gold standard endpoints to assess the state of mucosal disease, our data demonstrates that the two are not equivalent as their 'endoscopic categorical calls' are in agreement only 59% of the time. The data further shows that even after accounting for their known offset, their agreement is still only 80%. These results highlight the difference in the two currently accepted gold standards and elucidate the imperfections of using a subjective gold standard.

Example 6: Development and Validation of a Multi-Marker Serum Test for the Assessment of Mucosal Healing in Crohn's Disease Patients 748 serum samples obtained from 396 adult CD patients at or within 30 days of ileocolonoscopy (Tables 7-9) were retrospectively analyzed. Multiple logistic regression equations were used to mathematically model expression levels of a set of serum protein biomarkers (FIG. 1), selected from a larger set of markers, against visualized endoscopic disease severity as determined by CDEIS scores (Sipponen et al., Endoscopic evaluation of Crohn's disease activity: Comparison of the CDEIS and the SES-CD. Inflamm Bowel Dis, 2010, 16: 2131-2136; Sipponen et al., Crohn's disease activity assessed by fecal calprotectin and lactoferrin: correlation with Crohn's disease activity index and endoscopic findings. Inflamm Bowel Dis, 2008, 14: 40-46). The output of the MH model is a 0-100 scale termed as the Mucosal Healing Index (MHI). The model was independently validated in a prospectively collected, centrally read, longitudinal cohort of 118 patients (N=412 samples) from the TAILORIX clinical trial (Table 8). The final model utilized 13 biomarkers that represent biological pathways thought to be involved in the MH process including angiogenesis (Ang1, Ang2), growth factor signaling (TGFα), matrix remodeling (MMP-1, -2, -3, -9 and EMMPRIN), cell adhesion (CEACAM1, VCAM1), immune modulation (IL7), and inflammation (CRP, SAA1) (FIG. 1).

TABLE 7

| Clinical Cohorts | Cohort 1 (U Padua, Italy) | Cohort 2 (UCSD) | Cohort 3 (MSH, Toronto) | Cohort 4 (STORI) | Cohort 5 (TAILORIX) |
|---|---|---|---|---|---|
| Endoscopic Score | CDEIS | SES-CD | SES-CD | CDEIS | CDEIS |
| Patients (N) | 18 | 31 | 146 | 83 | 118 |
| Serum Samples (N) | 50 | 45 | 157 | 83 | 412 |

TABLE 8

Patient Characteristics

| | Training Set (Cohorts 1-4) | Validation Set (Cohort 5: TAILORIX) | p-Value |
|---|---|---|---|
| N | 278 | 118 | |
| Age (means in years (RANGE)] | 34 (18-74) | 34 (18-76) | 0.75 |
| Male Gender [n(%)] | 150 (54%) | 45 (38%) | 0.02* |
| Disease Location | | | 0.14 |
| ILEAL ONLY | 43 (27.4%) | 27 (22.9%) | |
| COLONIC ONLY | 38 (24.2%) | 20 (16.9%) | |
| ILEOCOLONIC | 76 (48.4%) | 71 (60.2%) | |
| Endoscopic Reading | Read at each center | Centrally Read | |
| Therapy | All Comers | IFX + IS | |

TABLE 9

Sample Characteristics

| | Training Set (Cohorts 1-4) | Validation Set (Cohort 5: TAILORIX) |
|---|---|---|
| N | 335 | 412 |
| Collection Type | Retrospective Cross-sectional | Prospective Longitudinal |
| Time From Nearest Endoscopy | | |
| 0 days | 147 (44%) | 132 (32%) |
| ≤30 days | 267 (80%) | 376 (91%) |
| Endoscopic Disease Severity Definitions | | |
| Severe (CDEIS >12) | 39 (11.6%) | 52 (12.6%) |
| Moderate (CDEIS 9-12) | 17 (5.1%) | 40 (9.7%) |
| Mild (CDEIS 3-8) | 120 (35.8%) | 146 (35.4%) |
| Remission (CDEIS <3) | 159 (47.5%) | 175 (42.4%) |

Figure 3A:
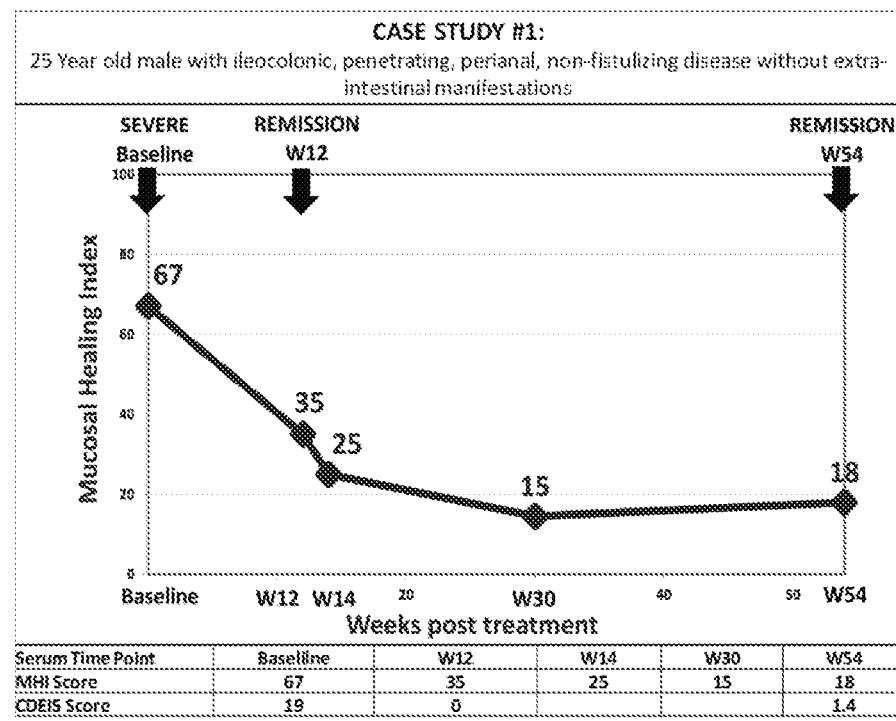
FIGS. 3A-3C show representative case studies from the validation cohort demonstrating the utility of the MHI as a monitoring tool. The MHI can monitor the status of mucosal health in Crohn's Disease patients.
Figure 3B:
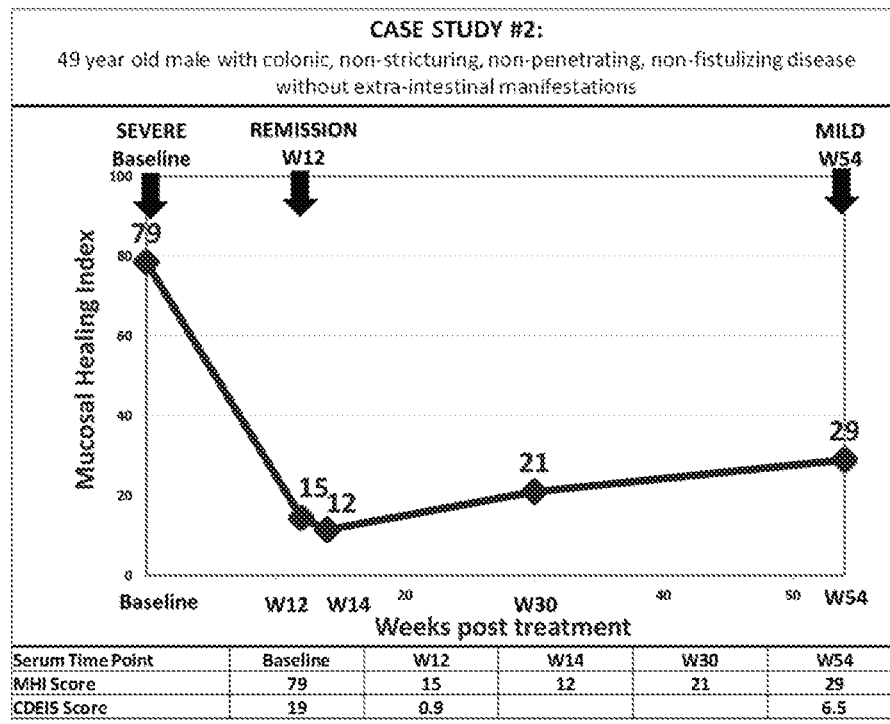
Figure 3C:
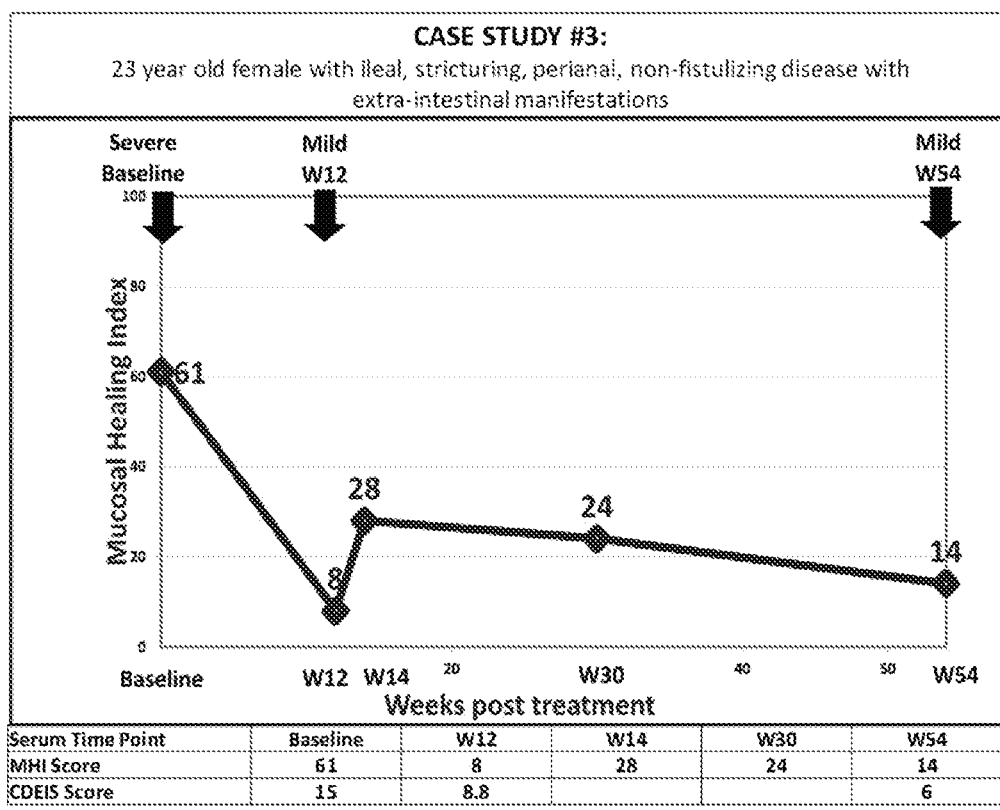

A total of 748 samples from 396 patients (mean age: 34 years, 49% males), were used to develop the MH test. Tables 7-9 describe the characteristics of the patients and samples used in the training and validation cohorts. The MH test included 13 biomarkers representing multiple biological pathways involved in maintaining mucosal homeostasis (FIG. 1). The output of the MH test is Mucosal Healing Index (MHI) score ranging from 0-100 (FIGS. 2A-2D). The overall accuracy of the MHI was 90% (FIGS. 2A-2D) with a negative predictive value (NPV) of 92% for identifying patients in remission (CDEIS <3) or with mild (CDEIS 3-8) endoscopic disease (MHI range 0-40) and a positive predictive value (PPV) of 87% for identifying patients with endoscopic evidence of active disease (CDEIS ≥3; MHI range 50-100). 14% of the specimens fell within an intermediate zone (MHI 41-49) with an observed 78% probability of active disease. MHI can be used in all CD patients regardless of disease location and the treatment options employed. MHI is a monitoring tool that can be used to longitudinally track the disease state of the intestinal mucosa in clinically diagnosed Crohn's Disease patients (FIGS. 3A-3C).

Example 7: A Non-Invasive Serological Test to Assess the Efficacy of Biologic and Non-Biologic Therapies on the Mucosal Health of Patients with Crohn's Disease The aim of the present study is to further validate the performance of the MH test in an independent cohort of patients with CD who have been treated with either biologic or non-biologic therapeutic options (i.e., therapeutic agnostic). This validation set is comprised of samples from five separate studies from geographically diverse regions in Europe, Canada and the United States (n=278 patients; Table 10). Therapy data was available for n=256 patients, which were used in the analysis.

TABLE 10

Collection Sites and Patients

|  | Total Patients |
|---|---|
| UCSD<br>Biologic and/or non-biologic | 124 |
| McGill U<br>Ustekinumab | 14 |
| U of Padua<br>anti-TNFα | 6 |
| Med Col Wisconsin<br>Vedolizumab | 22 |
| TAILORIX (Baseline)<br>anti-TNF naive | 112 |
|  | 278 |

Figure 4:
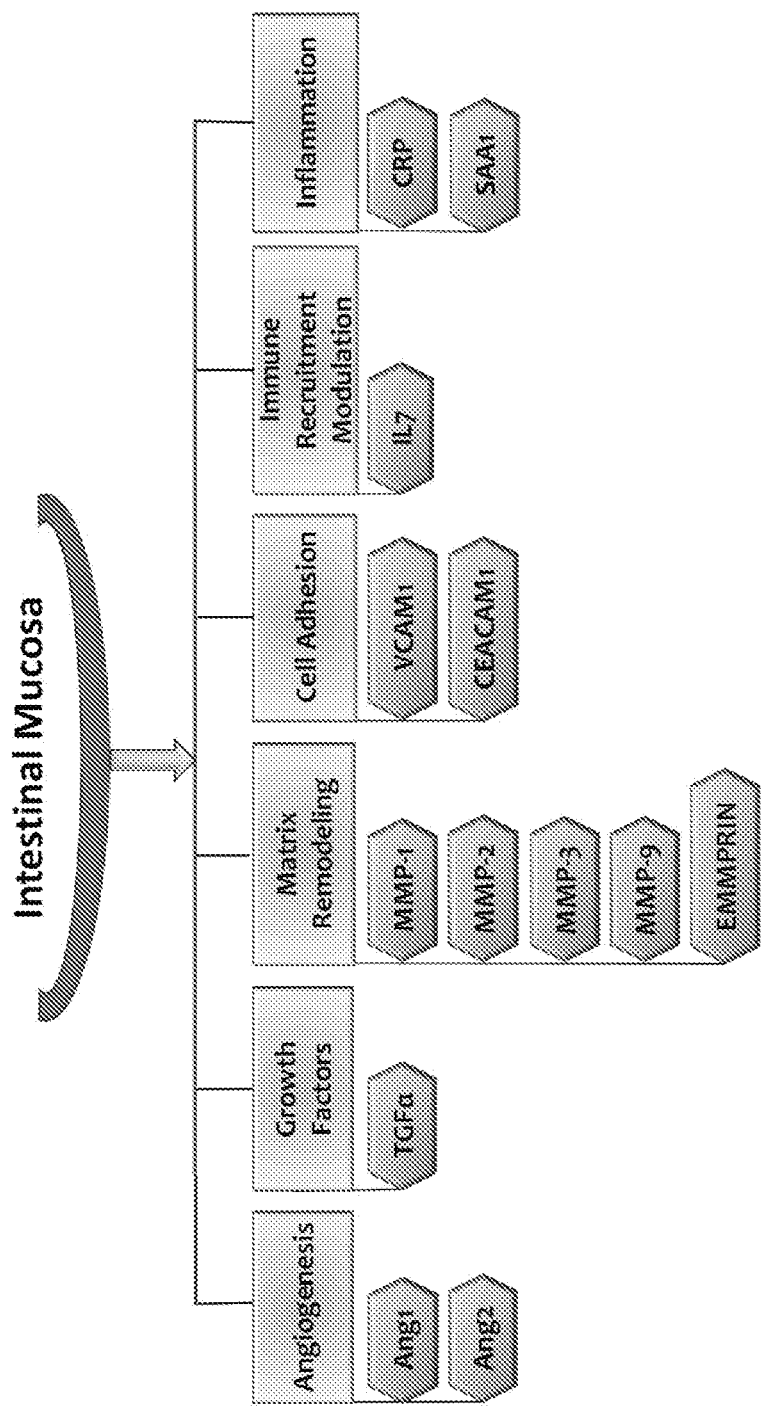
FIG. 4 shows mucosal healing test markers. Ang 1, 2, Angiotensin 1, 2; TGFα, Transforming Growth Factor alpha; MMP 1, 2, 3 & 9, Matrix Metalloproteinase 1, 2, 3, & 9; EMMPRIN, Extracellular Matrix Metalloproteinase Inducer; VCAM, Vascular Cell Adhesion Molecule; CEACAM, Carcinoembryonic Antigen-related Cell Adhesion Molecule; IL-7, Interleukin-7; CRP, C-Reactive Protein; SAA1, Serum Amyloid A1.
Figure 5:
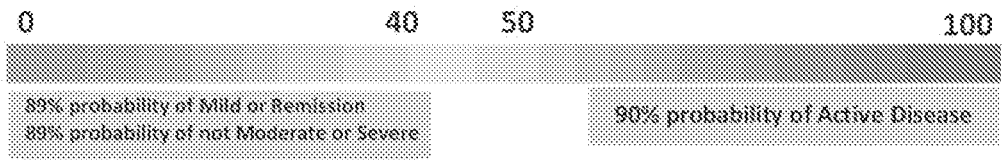
FIG. 5 shows MHI and assay performance. The MH test has high accuracy regardless of the treatment option.

An independent multi-center cross-sectional cohort study of CD patients. Endoscopic severity is categorized using the CDEIS, with active endoscopic disease being defined as a CDEIS ≥3 (SES-CD scores were converted to CDEIS; see, Example 8 below). The MH test is comprised of 13 biomarkers representing multiple biologic pathways in the MH process (FIG. 4). Logistic regression applied to data produces a 0-100 scale, termed as the Mucosal Healing Index (MHI) (FIG. 5). One-way ANOVA was used to determine mean differences in MHI across endoscopic disease severity categories. *$p<0.05$ was considered as significant.

Figure 6:
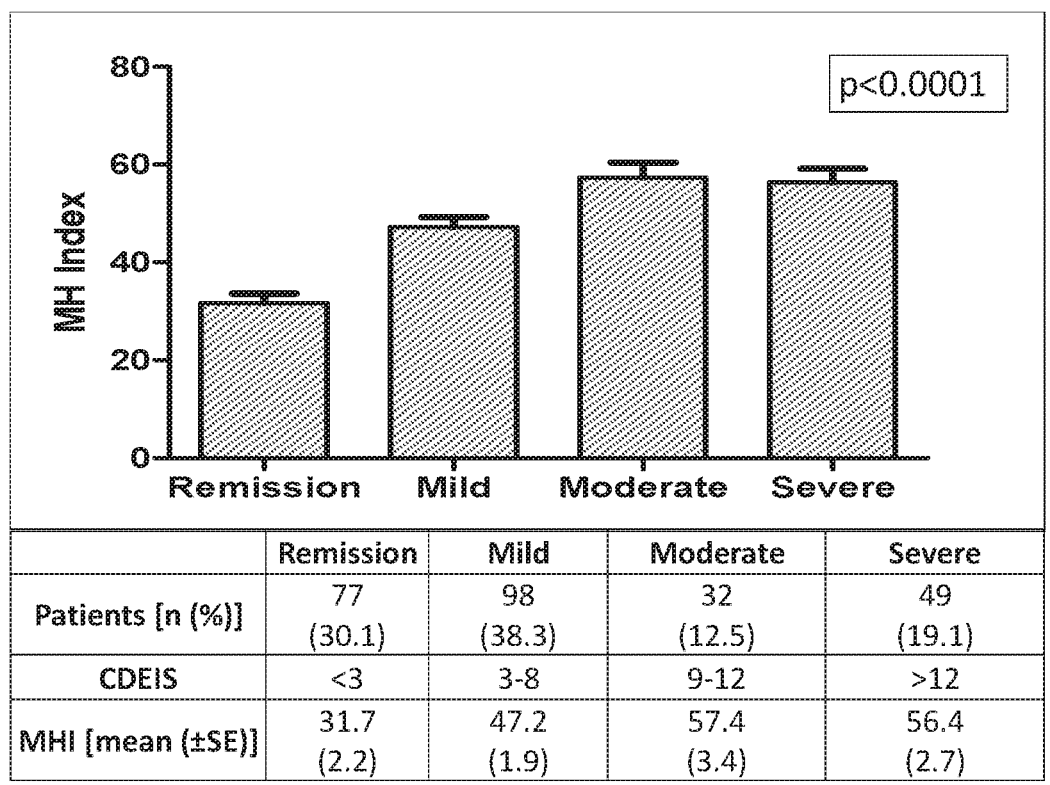
FIG. 6 shows MHI scores and endoscopic disease severity. MIR index increases with endoscopic disease activity.

The median age of patients was 34 years (range: 18-88; males: 43.9%). The patient population included all disease locations: ileal, ileo-colonic, and colonic. The MH test has performed equivalently in all CD patients regardless of disease location or treatment selection. Approximately 50% of the cohort consisted of patients treated with biologics: ADA: 18.3%, IFX: 15%, anti-integrins: 10.9%, UST: 6.5% (Table 11). 42% of the remaining were anti-TNFα naïve, on thiopurines, mesalamine or not on medications. The overall test accuracy in this CD patient population was 90%. The negative predictive value (NPV) was 89% for identifying patients in remission or mild endoscopic disease. The positive predictive value (PPV) was 90% for identifying patients with endoscopically active disease (CDEIS >3) (FIG. 5). Mean MHI values demonstrated significant correlation with increasing endoscopic disease severity (FIG. 6; Table 12). There was no significant change in accuracy of the test in patients treated with biologics vs non-biologics.

TABLE 11

Patient Data & Treatment

| Age [median (range)] | 34 (18-88) |
|---|---|
|  | N (%) |
| Male gender | 122 (43.9) |
| On Adalimumab | 51 (18.3) |
| On Infliximab | 42 (15) |
| On Vedolizumab | 27 (9.7) |
| On Ustekinumab | 18 (6.5) |
| On Certolizumab | 1 (0.4) |
| On Natalizumab | 1 (0.4) |
| On non-biologics | 116 (41.7) |

TABLE 12

Endoscopic Disease Severity Definitions

|  | N (%) |
|---|---|
| Severe (CDEIS: >12 or SES-CD: >15) | 49 (17.6) |
| Moderate (CDEIS: 9-12 or SES-CD: 7-15) | 33 (11.9) |
| Mild (CDEIS: 3-8 or SES-CD: 3-6) | 109 (39.2) |
| Remission (CDEIS: <3 or SES-CD: <3) | 87 (31.3) |

The MH test provides an objective index score that accurately assesses MH in CD patients across several different types of therapeutic classes and regardless of disease location. The test can be utilized as a non-invasive tool to measure, monitor and help manage the care of all CD patients regardless of therapy.

Example 8: Assessing the Variability Between Endoscopic Scoring Indices for Evaluation of Crohn's Disease Activity Crohn's disease endoscopic index of severity (CDEIS) and simple endoscopic score for Crohn's disease (SES-CD) are two commonly used validated endoscopic indices for assessing the state of mucosal disease in CD patients and to determine the outcome of clinical trials that utilize mucosal healing as an endpoint. Although CDEIS and SES-CD indices demonstrate a high correlation (Daperno et al., Gastrointestinal Endoscopy (2004) 60(4):505-512; Sipponen et al., Endoscopic evaluation of Crohn's disease activity: Comparison of the CDEIS and the SES-CD. Inflamm Bowel Dis, 2010, 16: 2131-2136), there are notable differences between the two indices (Table 13). Further, the disease severity groupings between them are not well aligned which can impact the interpretations of endoscopic disease activity outcomes (Sipponen et al., Inflamm Bowel Dis, 2010, 16: 2131-2136). A linear offset between CDEIS and SES-CD is widely accepted (Daperno et al., Gastrointestinal Endoscopy (2004) 60(4):505-512), but a closer look at the accuracy and impact of using the two scoring indices has not been adequately studied.

TABLE 13

|  | CDEIS<br>(Mary J Y et al., *Gut*,<br>1989, 30: 983-989) | SES-CD<br>(Daperno M et al., *GastroIntest. Endosc.*,<br>2004, 60: 505-512) |
|---|---|---|
| Scoring System<br>Development | First validated score for endoscopic<br>findings in patients with Crohn's Disease<br>CDEIS has served as the gold standard<br>for endoscopic scoring of CD lesions.<br>It is time-consuming, complicated, and<br>not well suited for routine clinical<br>practice. | Constructed from CDEIS<br>Attempt to simplify the CDEIS<br>Based on importance and reproducibility of<br>the most relevant endoscopic characteristics<br>of Crohn's Disease<br>Included only characteristics that were<br>contributing to clinical symptomatology |

TABLE 13-continued

| | CDEIS<br>(Mary J Y et al., *Gut*,<br>1989, 30: 983-989) | SES-CD<br>(Daperno M et al., *GastroIntest. Endosc.*,<br>2004, 60: 505-512) |
|---|---|---|
| Score Range | 0 to 44 | 0 to 56 |
| Endoscopic Variables Scored | 6 Variables<br>Presence of deep ulcers<br>Presence of superficial ulcers<br>Non-ulcerated stenosis<br>Ulcerated stenosis<br>Proportion of ulcerated surface<br>Proportion of ulcerated surface affected by disease | 4 Variables<br>Presence and size of ulcers<br>Proportion of surface covered by ulcers<br>Proportion of surface affected by disease<br>Presence and severity of stenosis |
| Evaluation of Ulcers | Based on depth | Based on size |
| Number of ileocolonic segments explored | Takes into account as the score summation is divided by the number of segments evaluated | Does not take into account |

The aim of this study was to compare the endoscopic disease severity as determined by the CDEIS and SES-CD indices in the TAILORIX clinical cohort (G. D'Haens, S. Vermiere, D. Laharie et. al. Drug-concentration verses symptom-driven dose adaptation of Infliximab in patients with active Crohn's disease: a prospective, randomized multicenter trial (TAILORIX) Oral Presentation, ECCO 2016).

Figure 7:
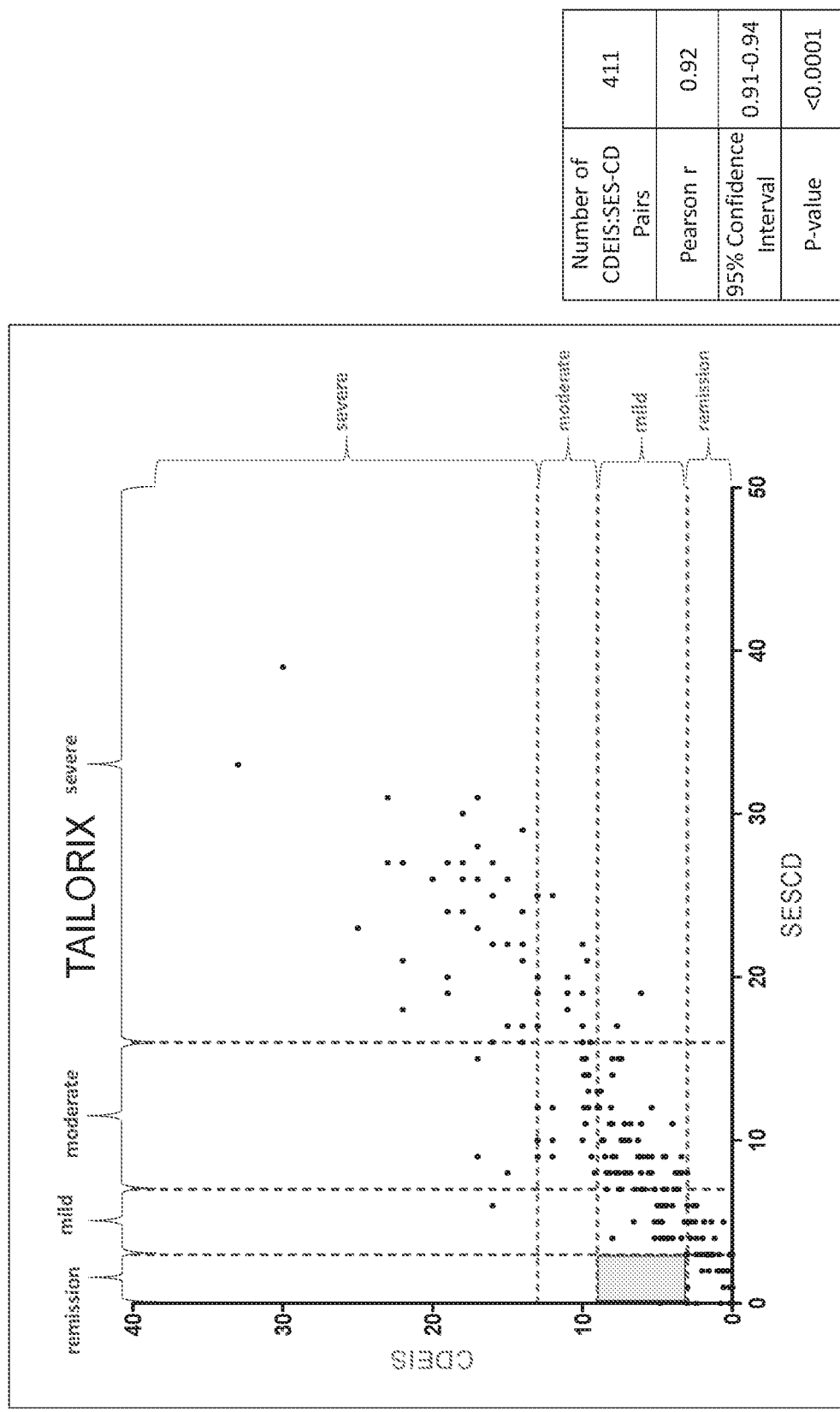
FIG. 7 shows CDEIS vs. SES-CD scores in the TAILORIX study. Endoscopic disease severity groupings mismatch between CDEIS and SES-CD indices. Centrally read CDEIS and SES-CD scores were collected at the same time from the same patients in the TAILORIX clinical trial. The two scores demonstrated an overall correlation of 92% (Pearson r=0.92) in agreement with previous reports (Daperno et al., Gastrointestinal Endoscopy (2004) 60(4):505-512; Sipponen et al., Endoscopic evaluation of Crohn's disease activity: Comparison of the CDEIS and the SES-CD. Inflamm Bowel Dis, 2010, 16: 2131-2136). However, 41% (170/411) endoscopic disease severity groupings were discordant between CDEIS and SES-CD using standard definitions for CDEIS and SES-CD scores (indicated by colored shaded areas). 33% (58/175) samples deemed as endoscopic remission with CDEIS were indicated to have active disease by SES-CD (FIG. 8A).

Both CDEIS and SES-CD scores were collected at the same time, in a centrally read, prospectively collected, longitudinal cohort of 118 CD patients in the TAILORIX clinical trial (FIG. 7). Up to three endoscopic scores were available from each patient over a period of one year. Standard disease severity definitions were applied to both CDEIS and SES-CD scores. CDEIS scores (Sipponen et al., Inflamm Bowel Dis, 2010, 16: 2131-2136; Sipponen et al., Crohn's disease activity assessed by fecal calprotectin and lactoferrin: correlation with Crohn's disease activity index and endoscopic findings. Inflamm Bowel Dis, 2008, 14: 40-46) were classified as remission <3, mild 3-8, moderate 9-12, and severe >12. For SES-CD (Moskovitz et al., Defining and validating cut-offs for the Simple Endoscopic Score for Crohn's Disease. Gastroenterology, 2007, 132: S1097), the same groups were defined as <3, 3-6, 7-15, and >15, respectively. Using the TAILORIX data, a linear regression equation was derived to predict corresponding CDEIS scores from SES-CD scores.

Figures 8A, 8B:
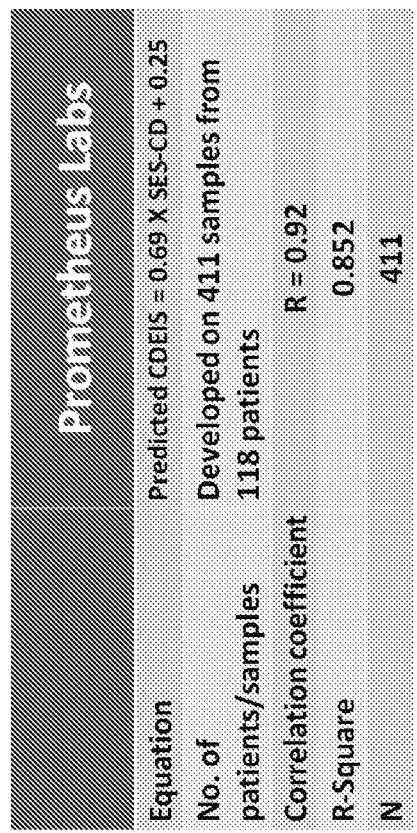
FIGS. 8A-8B show contingency tables pre- and post-normalization of CDEIS and SES-CD scores. Agreement between endoscopic disease severity groupings of CDEIS and SES-CD improves to only 80% even after normalization.

Using the raw CDEIS and SES-CD scores, a contingency table (FIG. 8A) shows the overall agreement in disease severity states (Remission, Mild, Moderate and Severe) is only 59% (241/411). 33% ($58/175$) of the scores deemed as disease in remission by CDEIS are classified as active disease by SES-CD. Likewise, $81/146$ (~56%) of mild disease classifications by CDEIS were suggested to have moderate disease with SES-CD. After applying the observed linear regression equation (CDEIS=0.69*SES-CD+0.25; r=0.92) to normalize the two scores the overall agreement improved to 80% (328/411) (FIG. 8B).

While CDEIS and SES-CD scores correlate well and are utilized independently as endoscopic gold standard endpoints, the data demonstrates that the two are not equivalent as their 'endoscopic categorical calls' are in agreement only 59% of the time. Even after accounting for their known offset, the agreement is still only 80% (328/411) (FIG. 8B). These results highlight the difference in the two currently accepted gold standards and elucidate the importance and clinical unmet need for establishing a single objective score to assess the mucosal state in patients with CD.

Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of treating Ulcerative Colitis (UC) in a patient the method comprising:
   (a) determining a Mucosal Healing Index (MHI) score for the patient by:
      (i) detecting in a serum sample from the patient with UC expression levels of biomarkers consisting of Angiotensin 1 (Ang1), Angiotensin 2 (Ang2), Carcinoembryonic Antigen-related Cell Adhesion Molecule (CEACAM1), Vascular Cell Adhesion Molecule 1 (VCAM1), Transforming Growth Factor alpha (TGFα), C-Reactive Protein (CRP), Serum Amyloid A1 (SAA1), Matrix Metalloproteinase 1 (MMP-1), Matrix Metalloproteinase 2 (MMP-2), Matrix Metalloproteinase 3 (MMP-3), Matrix Metalloproteinase 9 (MMP-9), Extracellular Matrix Metalloproteinase Inducer (EMMPRIN), and (Interleukin 7 (IL-7); and
      (ii) applying a mathematical algorithm to the expression levels of the biomarkers, thereby producing the MHI score for the patient; and
      (iii) identifying the MHI score for the patient as comprising greater than or equal to 50 on a scale from 0 to 100; and
   (b) administering a therapeutically effective amount of a therapeutic agent to treat the UC in the patient based, at least in part, on the MHI score.

2. The method of claim 1, wherein the detecting comprises contacting the serum sample with a binding partner for each of the biomarkers and detecting binding between each of the biomarkers and the binding partner.

3. The method of claim 2, wherein the binding partner is an antibody.

4. The method of claim 1, further comprising:
   determining that the patient has a high probability of being in remission or having mild endoscopic disease when the MHI score is less than or equal to 40 on a scale from 0 to 100.

5. The method of claim 1, further comprising:
   determining that the patient has a high probability of having endoscopically active disease based on the MHI score comprising greater than or equal to 50 on a scale from 0 to 100.

6. The method of claim 1, further comprising:
   determining that the patient has a moderate probability of having endoscopically active disease when the MHI score is between 40 and 50 on a scale from 0 to 100.

7. The method of claim 1, wherein the mathematical algorithm comprises two or more models relating the expression levels of the biomarkers to an endoscopic score.

8. The method of claim 7, wherein one or more of the two or more models are derived by (i) using one or more classification and regression trees, or (ii) using an ordinary least squares regression to model diagnostic specificity, or a combination thereof.

9. The method of claim 7, wherein one or more of the two or more models are derived by (i) using random forest learning classification, or (ii) using quantile classification, or a combination thereof.

10. The method of claim 7, wherein one or more of the two or more models are derived by (i) using logistic regression to model diagnostic sensitivity, or (ii) using logistic regression to model diagnostic specificity, or a combination thereof.

11. A method for treating Ulcerative Colitis (UC) in a patient, the method comprising:
   (a) identifying a patient with UC having a Mucosal Healing Index (MHI) score of between 50-100 on a scale of 0-100, wherein the MHI score is determined by applying a mathematical algorithm to expression levels of biomarkers detected in a serum sample from the patient, wherein the biomarkers consist of Angiotensin 1 (Ang1), Angiotensin 2 (Ang2), Carcinoembryonic Antigen-related Cell Adhesion Molecule (CEACAM1), Vascular Cell Adhesion Molecule 1 (VCAM1), Transforming Growth Factor alpha (TGFα), C-Reactive Protein (CRP), Serum Amyloid A1 (SAA1), Matrix Metalloproteinase 1 (MMP-1), Matrix Metalloproteinase 2 (MMP-2), Matrix Metalloproteinase 3 (MMP-3), Matrix Metalloproteinase 9 (MMP-9), Extracellular Matrix Metalloproteinase Inducer (EMMPRIN), and (Interleukin 7 (IL-7); and
   (b) administering a therapeutically effective amount of a therapeutic agent to the patient for treatment of the UC.

12. The method of claim 11, wherein the therapeutic agent comprises biologic or non-biologic therapy.

13. The method of claim 12, further comprising: determining efficacy of the biologic or non-biologic therapy.

14. The method of claim 11, wherein the MHI score assesses mucosal healing at colonic, ileocolonic, and/or ileal disease locations in the patient.

15. The method of claim 11, wherein the MHI score assesses mucosal healing in the patient after surgery.

16. The method of claim 15, wherein the MHI score assesses mucosal healing by identifying post-operative, endoscopic recurrence in the patient.

17. The method of claim 11, wherein the patient is in remission or has mild endoscopic disease when the MHI score is between 0-40, wherein the remission corresponds to an endoscopic index of severity of less than 3.

18. The method of claim 17, wherein the mild endoscopic disease corresponds to an endoscopic index of severity of between 3-8.

19. The method of claim 11, wherein the patient has endoscopically active disease when the MHI score is between 50-100, wherein the endoscopically active disease corresponds to an endoscopic index of severity of greater than or equal to 3.

20. The method of claim 11, wherein the MHI score assesses mucosal healing by predicting or monitoring the mucosal status in the patient.

\* \* \* \* \*